(12) United States Patent
Fekete et al.

(10) Patent No.: US 12,239,125 B2
(45) Date of Patent: Mar. 4, 2025

(54) COMPOSITIONS FOR ORGAN PRESERVATION

(71) Applicant: SigmaDrugs Kutató Korlátolt Felelösségü Társaság, Budapest (HU)

(72) Inventors: Andrea Fekete, Budapest (HU); Ádám Vannay, Budapest (HU); Ádám Hosszú, Budapest (HU)

(73) Assignee: SigmaDrugs Kutató Korlátolt Felelsség Társaság, Budapest (HU)

( * ) Notice: Subject to any disclaimer, the term of this patent is extended or adjusted under 35 U.S.C. 154(b) by 317 days.

(21) Appl. No.: 16/463,944

(22) PCT Filed: Nov. 24, 2017

(86) PCT No.: PCT/HU2017/050051
§ 371 (c)(1),
(2) Date: May 24, 2019

(87) PCT Pub. No.: WO2018/096376
PCT Pub. Date: May 31, 2018

(65) Prior Publication Data
US 2019/0335745 A1   Nov. 7, 2019

(30) Foreign Application Priority Data
Nov. 24, 2016   (HU) .................................. P1600639

(51) Int. Cl.
| | | |
|---|---|---|
| A61K 31/138 | (2006.01) | |
| A01N 1/02 | (2006.01) | |
| A61K 31/40 | (2006.01) | |
| A61K 31/44 | (2006.01) | |
| C07C 211/03 | (2006.01) | |
| C07D 207/04 | (2006.01) | |
| C07D 207/18 | (2006.01) | |
| C07D 207/30 | (2006.01) | |
| C07D 211/04 | (2006.01) | |
| C07D 213/04 | (2006.01) | |

(52) U.S. Cl.
CPC .......... *A01N 1/0226* (2013.01); *A61K 31/138* (2013.01); *A61K 31/40* (2013.01); *A61K 31/44* (2013.01); *C07C 211/03* (2013.01); *C07D 207/04* (2013.01); *C07D 207/18* (2013.01); *C07D 207/30* (2013.01); *C07D 211/04* (2013.01); *C07D 213/04* (2013.01)

(58) Field of Classification Search
CPC ...... A61K 31/138; A61K 31/40; A61K 31/44; A01N 1/0226; C07C 211/03; C07D 207/04; C07D 207/18; C07D 207/30; C07D 211/04; C07D 213/04
See application file for complete search history.

(56) References Cited

U.S. PATENT DOCUMENTS

| | | | |
|---|---|---|---|
| 6,245,781 | B1 | 6/2001 | Upadhyay et al. |
| 6,297,212 | B1 | 10/2001 | Fahy |
| 10,124,006 | B2 | 11/2018 | Fekete et al. |
| 10,842,794 | B2 | 11/2020 | Fekete et al. |
| 2008/0286747 | A1 | 11/2008 | Curtis et al. |
| 2011/0270215 | A1 | 11/2011 | Steen |
| 2011/0281794 | A1 | 11/2011 | Steen |
| 2012/0172363 | A1 | 7/2012 | Smith et al. |
| 2013/0065218 | A1 | 3/2013 | Steen |
| 2014/0255905 | A1 | 9/2014 | Steen |
| 2017/0295776 | A1 | 10/2017 | Hoehn et al. |

FOREIGN PATENT DOCUMENTS

| | | | | |
|---|---|---|---|---|
| WO | WO-2011142705 A1 | * | 11/2011 | ............ A01N 1/0226 |
| WO | WO-2013076245 A1 | * | 5/2013 | ............ A61K 31/137 |

OTHER PUBLICATIONS

Klouz et al.: "Protection of cellular and mitochondrial functions against liver ischemia by N-benzyl-N'-(2-hydroxy-3,4-dimethoxybenzyl)-piperazine (BHDP), a sigma1 ligand", Eur J Pharmacol, 2008, vol. 578, pp. 292-299.

Sharkey et al.: "Cocaine binding at sigma receptors", Eur J of Pharmacology, 1988, vol. 149, pp. 171-174.

* cited by examiner

*Primary Examiner* — Sun Jae Yoo
(74) *Attorney, Agent, or Firm* — Jason D. Voight

(57) ABSTRACT

The invention relates to the field of preserving the viability of organs or tissues to be transplanted into a recipient in need of such a transplantation. In particular, the invention relates to use of a sigma 1 receptor agonist compound in preservation solutions and preservation solutions comprising a sigma 1 receptor agonist compound.

21 Claims, 21 Drawing Sheets
Specification includes a Sequence Listing.

D/1 SHA

ATx VEH

ATx

ATx

D/1    SHAM

D/2    ATx VEH

ATx VEH

ATx FLU

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Rat Lcn2 forward primer

<400> SEQUENCE: 1
gggctgtccg atgaactgaa                                        20

<210> SEQ ID NO 2
<211> LENGTH: 20
<212> TYPE: DNA
<213> ORGANISM: Artificial Sequence
<220> FEATURE:
<223> OTHER INFORMATION: Rat Lcn2 reverse primer

<400> SEQUENCE: 2
cattggtcgg tgggaacaga                                        20

<210> SEQ ID NO 3
<211> LENGTH: 20
<212> TYPE: DNA
<213> ORGANISM: Artificial Sequence
<220> FEATURE:
<223> OTHER INFORMATION: Rat Kim1 forward primer

<400> SEQUENCE: 3
cgcagagaaa cccgactaag                                        20

<210> SEQ ID NO 4
<211> LENGTH: 20
<212> TYPE: DNA
<213> ORGANISM: Artificial Sequence
<220> FEATURE:
<223> OTHER INFORMATION: Rat Kim1 reverse primer

<400> SEQUENCE: 4
caaagctcag agaccccatc                                        20

<210> SEQ ID NO 5
<211> LENGTH: 20
<212> TYPE: DNA
<213> ORGANISM: Artificial Sequence
<220> FEATURE:
<223> OTHER INFORMATION: Rat Mcp1 forward primer

<400> SEQUENCE: 5
atgcagttaa tgccccactc                                        20

<210> SEQ ID NO 6
<211> LENGTH: 20
<212> TYPE: DNA
<213> ORGANISM: Artificial Sequence
<220> FEATURE:
<223> OTHER INFORMATION: Rat Mcp1 reverse primer

<400> SEQUENCE: 6
ttccttattg gggtcaccac                                        20

<210> SEQ ID NO 7
<211> LENGTH: 24
<212> TYPE: DNA
<213> ORGANISM: Artificial Sequence

```
<220> FEATURE:
<223> OTHER INFORMATION: Rat Il1a forward primer

<400> SEQUENCE: 7
tctgccattg accatctgtc tctg                                          24

<210> SEQ ID NO 8
<211> LENGTH: 20
<212> TYPE: DNA
<213> ORGANISM: Artificial Sequence
<220> FEATURE:
<223> OTHER INFORMATION: Rat Il1a reverse primer

<400> SEQUENCE: 8
accacccggc tctccttgaa                                               20

<210> SEQ ID NO 9
<211> LENGTH: 20
<212> TYPE: DNA
<213> ORGANISM: Artificial Sequence
<220> FEATURE:
<223> OTHER INFORMATION: Rat Il6 forward primer

<400> SEQUENCE: 9
gccactgcct tccctacttc                                               20

<210> SEQ ID NO 10
<211> LENGTH: 22
<212> TYPE: DNA
<213> ORGANISM: Artificial Sequence
<220> FEATURE:
<223> OTHER INFORMATION: Rat Il6 reverse primer

<400> SEQUENCE: 10
gccattgcac aactcttttc tc                                            22

<210> SEQ ID NO 11
<211> LENGTH: 23
<212> TYPE: DNA
<213> ORGANISM: Artificial Sequence
<220> FEATURE:
<223> OTHER INFORMATION: Rat Il10 forward primer

<400> SEQUENCE: 11
agaaccatgg cccagaaatc aag                                           23

<210> SEQ ID NO 12
<211> LENGTH: 23
<212> TYPE: DNA
<213> ORGANISM: Artificial Sequence
<220> FEATURE:
<223> OTHER INFORMATION: Rat Il10 reverse primer

<400> SEQUENCE: 12 acagggaga atcgatgac agc                                             23

<210> SEQ ID NO 13
<211> LENGTH: 21
<212> TYPE: DNA
<213> ORGANISM: Artificial Sequence
<220> FEATURE:
<223> OTHER INFORMATION: Rat TNFa forward primer

<400> SEQUENCE: 13
ggggccacca cgctcttctg t                                             21
```

```
<210> SEQ ID NO 14
<211> LENGTH: 24
<212> TYPE: DNA
<213> ORGANISM: Artificial Sequence
<220> FEATURE:
<223> OTHER INFORMATION: Rat TNFa reverse primer

<400> SEQUENCE: 14
ctccgcttgg tggtttgcta cgac                                          24

<210> SEQ ID NO 15
<211> LENGTH: 23
<212> TYPE: DNA
<213> ORGANISM: Artificial Sequence
<220> FEATURE:
<223> OTHER INFORMATION: Rat Hmox1 forward primer

<400> SEQUENCE: 15
agaccgcctt cctgctcaac att                                           23

<210> SEQ ID NO 16
<211> LENGTH: 22
<212> TYPE: DNA
<213> ORGANISM: Artificial Sequence
<220> FEATURE:
<223> OTHER INFORMATION: Rat Hmox1 reverse primer

<400> SEQUENCE: 16
gattttcctc ggggcgtctc tg                                            22

<210> SEQ ID NO 17
<211> LENGTH: 21
<212> TYPE: DNA
<213> ORGANISM: Artificial Sequence
<220> FEATURE:
<223> OTHER INFORMATION: Rat Bax forward primer

<400> SEQUENCE: 17
agccgcccca ggacgcatcc a                                             21

<210> SEQ ID NO 18
<211> LENGTH: 24
<212> TYPE: DNA
<213> ORGANISM: Artificial Sequence
<220> FEATURE:
<223> OTHER INFORMATION: Rat Bax reverse primer

<400> SEQUENCE: 18
cagccgctcc cggaggaagt ccag                                          24

<210> SEQ ID NO 19
<211> LENGTH: 22
<212> TYPE: DNA
<213> ORGANISM: Artificial Sequence
<220> FEATURE:
<223> OTHER INFORMATION: Rat Bcl forward primer

<400> SEQUENCE: 19
atggcgcaag ccgggagaac ag                                            22

<210> SEQ ID NO 20
<211> LENGTH: 22
<212> TYPE: DNA
<213> ORGANISM: Artificial Sequence
<220> FEATURE:
<223> OTHER INFORMATION: Rat Bcl reverse primer
```

```
<400> SEQUENCE: 20
tggcgacaag gggccgtaga gg                                          22

<210> SEQ ID NO 21
<211> LENGTH: 24
<212> TYPE: DNA
<213> ORGANISM: Artificial Sequence
<220> FEATURE:
<223> OTHER INFORMATION: Rat Rn18S  forward primer

<400> SEQUENCE: 21
gcggtcgccg tcccccaact tctt                                        24

<210> SEQ ID NO 22
<211> LENGTH: 23
<212> TYPE: DNA
<213> ORGANISM: Artificial Sequence
<220> FEATURE:
<223> OTHER INFORMATION: Rat Rn18S  reverse primer

<400> SEQUENCE: 22
gcgcgtgcag ccccggacat cta                                         23

<210> SEQ ID NO 23
<211> LENGTH: 24
<212> TYPE: DNA
<213> ORGANISM: Artificial Sequence
<220> FEATURE:
<223> OTHER INFORMATION: Rat Actb  forward primer

<400> SEQUENCE: 23
accgagcatg gctacagcgt cacc                                        24

<210> SEQ ID NO 24
<211> LENGTH: 24
<212> TYPE: DNA
<213> ORGANISM: Artificial Sequence
<220> FEATURE:
<223> OTHER INFORMATION: Rat Actb  reverse primer

<400> SEQUENCE: 24
gtggccatct cttgctcgga gtct                                        24
```

COMPOSITIONS FOR ORGAN PRESERVATION

This is the national stage of International Application PCT/HU2017/050051, filed Nov. 24, 2017.

FIELD OF THE INVENTION

The invention relates to the field of preserving the viability of organs or tissues to be transplanted in a recipient in need of such a transplantation. In particular, the invention relates to the use of a sigma 1 receptor agonist compound in preservation solutions and preservation solutions comprising a sigma 1 receptor agonist compound.

BACKGROUND OF THE INVENTION

Organ transplantation is the only or primary treatment for several chronic diseases resulting in an end state organ failure, such as end stage renal disease (ESRD). Organ transplantation in these cases is associated with improved survival and quality of life.

The isolation of an organ from the systemic circulation, storage, and transplantation cause profound changes in the homeostasis and metabolism of the organ. Altered homeostasis and metabolism result in damages which may cause the deterioration of the organ, its later incompatibility with the recipient or—in case of the kidney—delayed graft function.

Organs are typically stored before transplantation (Tx) and must be kept viable during storage and transport. As soon as the organ is separated from the circulatory system, ischemic damage is inevitable. Inflammatory processes immediately take place and lead to structural and metabolic injury, and eventually to cell death. Depletion of the cellular energy stores, which happens as short as within a few hours after isolation, leads to a defect in ion pump function, edema, swelling of the cells.

Damages due to the lack of balance between the intracellular and the extracellular milieu are more or less addressed by the use of preservation solutions. Preservation solutions vary in composition, however, all aim to prevent cellular edema, to delay cell destruction, and to maximize organ function after perfusion is reestablished. A comparison of the composition of preservation solutions can be found in Guibert et al Organ Preservation: Current Concepts and New Strategies for the Next Decade Transfus Med Hemother 2011; 38:125-142.

The University of Wisconsin (UW) and Histidine-tryptophane-ketoglutarate (HTK or Custodiol) solution solution are the most widely used preservation fluid in pancreas, heart, kidney and lung preservation with comparable effects. Both have been shown to be comparable in liver and kidney preservation and also effective in cardiac surgery. HTK preservation was associated with an increased risk of graft loss with cold ischaemia time over 8 h (Stewart Z A, Cameron A M, Singer A L, Montgomery R A, Segev D L: Histidine-Tryptophan-Ketoglutarate (HTK) is associated with reduced graft survival in deceased donor livers, especially those donated after cardiac death. Am J Transplant 2009; 9:286-293.)

To prolong viability of the organ, oxygen and energy demand are to be kept at a minimum. Hypothermic storage is currently the primary means for preserving viability. Cooling itself, however, has detrimental effects on the tissue, due to e.g. oxidative stress and inflammation. Cold ischemia (or cold storage) time is an independent risk factor of delayed graft function and primary organ dysfunction (Erkasap S, Ates E. L-Arginine-enriched preservation solution decreases ischaemia/reperfusion injury in canine kidneys after long term cold storage. Nephrology Dialysis Transplant 2000; 15: 1224-7). Castaneda et al. have demonstrated that human cadaveric renal transplants have significantly more apoptotic cells than living-related transplants. The degree of apoptosis correlated significantly with the duration of cold ischemia (Castaneda M P, Swiatecka-Urban A, Mitsnefes M M et al. Activation of mitochondrial apoptotic pathways in human renal allografts after ischemia reperfusion injury. Transplantation 2003; 76: 50-54). Jani et al. demonstrated in a porcine model of that in DCD kidneys, warm ischaemia preferentially activates caspase-1, whereas cold ischaemia activates caspase-3 (Jani A, Zimmerman M, Martin J, Lu L, Turkmen K, Ravichandran K, Pacic A, Ljubanović D, Edelstein C L. Perfusion storage reduces apoptosis in a porcine kidney model of donation after cardiac death. Transplantation. 2011; 91:169-175). It has been shown by several authors that organs from extended criteria donors and non heart beating donors are particularly susceptible to injury during hypothermic preservation and may benefit from alternative methods of preservation (Stubenitsky et al. Kidney preservation in the next millenium Transpl Int (1999) 12:83-91). A switch to normothermic preservation is suggested by some, not only to prevent additional cold storage injury, but also to maintain cellular reparative mechanisms. Heat shock proteins are suggested to play a key role in the prevention of ischemic results (Moers et al. Non-heart beating organ donation: overview and future perspectives Transplant International doi: 10.1111/j.1432-2277.2007.00455.x)

The primary renal replacement treatment option for ESRD is kidney transplantation (KTx); which is associated with improved survival and quality of life. In a recent review of 110 studies including almost 2 million participants with kidney failure, KTx was associated with reduced risk of mortality and cardiovascular events as well as better quality of life than treatment with chronic dialysis.

While the number of kidney transplants has not changed in the past decade, the total number of patients living with a functioning kidney transplant continues to grow (*US Renal Data System Annual Report* 2015). One-year graft survival is 97% for living donor and 92% for deceased donor transplant recipients.

Living donor transplants have superior outcomes as these donors are usually younger and healthier. Cold ischemia time can be markedly reduced also as these Txs can be planned in advance. Graft survival can be further improved by performing preemptive Tx, transplanting when the recipient is in the best medical and social condition. Beside the obvious advantages of living donor Tx, the possible harm of a healthy person should always be considered as well.

Roughly one third of kidney transplants are from living donors in the US, while this number is around only 12% in Hungary. Hungary joined the Eurotransplant Foundation in 2012. This is a network of 8 countries with an aim to mediate and improve the allocation and distribution of donor organs for Tx.

Although short-term outcomes of KTx have improved substantially due to advances in surgical technique and immunosuppression, long-term outcomes have remained largely unchanged over the past decades. The factors affecting long-term outcome may be either alloantigen-dependent (e.g. HLA matching, HLA immunization etc.) or alloantigen-independent (e.g. donor type and age of both the donor and recipient), disease recurrence, comorbidities or time on dialysis). Among alloantigen-independent factors ischemia/reperfusion injury (IRI) is a major complication that has special influence on long-term survival after KTx. IRI is unavoidable and the duration of storage and cold ischemia time correlate with delayed graft function.

Treatment: Although effective immunosuppressive regimen is the key to successful Tx, immunosuppressants also have several undesirable effects on the kidney. They may provoke or reactivate infections (e.g. severe polyoma BK virus, cytomegalovirus and herpes viruses resulting in interstitial nephritis, or urinary tract infections, etc.). Calcineurin-inhibitors (tacrolimus and cyclosporin A) are nephrotoxic by causing persistent vasoconstriction, interstitial fibrosis and tubular atrophy that can eventually lead to chronic graft dysfunction. Mainly due to steroids tacrolimus, and mTOR inhibitors about a quarter of KTx patients develop 'de novo' post-transplant DM, which can lead to DNP and graft dysfunction. For all these reasons continuous and tight control of the immunsuppressive protocol is of special interest during post-transplant nephrological care.

The time of safely preserving the viability of a transplantable organ depends on the organ, the preservation method and solution used, and the condition of the organ. Prolongation of preservation time—either warm or cold—is of paramount importance.

Klouz et al. has found that BHDP (N-benzyl-N'-(2-hydroxy-3,4-dimethoxybenzyl)-piperazine), a sigmal ligand protected mitochondrial functions when administered to rats or when used in the preservation liquid of isolated liver (Kloutz et al. Protection of cellular and mitochondrial functions against liver ischemia by N-benzyl-N'-(2-hydroxy-3,4-dimethoxybenzyl)-piperazine (BHDP), a sigmal ligand. Eur J Pharmacol 578 (2008) 292-299.). It was not investigated whether BHDP acts as an agonist or antagonist. The authors suggest that BHDP protects liver cells and in particular mitochondria, and hypothesize that this may be related to the action of BHDP on mitochondrial sigma 1 receptors, however, admit that further studies are needed to validate or to reject this hypothesis. The authors do not suggest that BHDP should be used in organ preservation solutions, but rather an exhaustive research programme to validate or to reject their hypothesis. Furthermore, no transplantation has been performed by Klouz et al.

It has been surprisingly found that S1R agonist compounds, when used ex vivo in the preservation solution of a transplantable organ, prolong storage time of the organ and protect against functional and cellular damage in said organ as indicated by improved function and cellular integrity after autotransplantation of said organ.

BRIEF DESCRIPTION OF THE INVENTION

The invention is defined by the following paragraphs and the claims.

Ex vivo use of a sigma 1 receptor (S1R) agonist compound for reducing, delaying or preventing cellular damage during storage of a transplantable whole or partial organ or tissue stored in a preservation solution, wherein said S1R agonist compound is comprised in said preservation solution In a preferred embodiment structural and/or functional damage of the whole or partial organ or tissue is ameliorated compared to the detected, measured, expected or predicted structural and/or functional damage of the whole or partial organ or the tissue stored under the same conditions and in the same preservation solution not comprising the S1R agonist compound, wherein the structural and/or functional damage of the whole or partial organ or tissue is associated with cellular damage caused by the ex vivo storage. In preferred embodiments the structural and/or functional damage of the whole or partial organ or tissue is ameliorated by at least 15%, at least 25%, at least 50%. Amelioration is measured, preferably in a quantitative manner, by the change of a marker characteristic of the structural and/or functional damage.

In a preferred embodiment the cellular damage is associated with an altered level of organ specific biomarker(s) or with a condition of the whole or partial organ or tissue selected from functional impairment and structural damage.

In a preferred embodiment the cellular damage is caused by the ex vivo storage and is associated with an altered level of one or more marker(s) selected from chaperones, vasoactive agents, markers of apoptotic pathways, markers of necrotic pathways, markers of inflammation, markers of activation of the immune system, markers of endoplasmatic reticulum stress, markers of oxidative stress, markers of angiogenesis, markers of remodelling, markers of regeneration.

Cellular damage caused by storage contributes to graft rejection, delayed graft function, graft loss, decreased graft functionality and decreased survival after transplantation.

The temperature of storage may be a temperature approximately the temperature characteristic for the species the organ or tissue belongs to, i.e. normothermic storage. The temperature of storage may be below or at least 5° C., below or at least 10° C., below core temperature characteristic for the species the organ or tissue belongs to, and is preferably from 0° C.-10° C., more preferably from 0° C.-4° C., highly preferably 4° C. In a preferred embodiment the whole or partial organ or tissue is stored at a temperature of 0 to 10° C.

Maximum preservation time of said whole or partial organ or tissue is preferably increased compared to the predicted or generally accepted or statistically assessed maximum preservation time of the whole or partial organ or the tissue, respectively, stored under the same conditions and in the same preservation solution not comprising the S1R agonist compound. Maximal preservation time may be increased, in particular increased by at least 15%, at least 25%, preferably least 50% and highly preferably at least 100%.

The time of storage may be, in particular, at least 1 h, or at least 3 h or at least 6 h or preferably the time of storage may be several days (e.g. 3 days or 2 days).

The organ or tissue may be any transplantable organ or tissue, including artificial tissues or organs and tissues or organs produced by a cell culture based method. The organ may be selected from heart, lung and abdominal organs, including liver, pancreas, intestine, kidney; skin, eye, bone marrow. The tissue may be skin tissue, blood vessel tissue, islets of Langerhans, renal tissue, lung tissue, heart tissue, cornea etc. The organ may be a partial organ, e.g. a liver lobe, a lung lobe. Preferably, the organ is an abdominal organ. Highly preferably, the organ is the kidney or the liver.

1. In an embodiment the compound is an S1R agonist compound wherein said compound is an agonist selective for S1R over S2R (sigma 2 receptor), i.e. the compound is a selective S1R agonist. A compound is selective for S1R over S2R if it has a higher affinity for S1R than S2R, preferably an at least 5 times higher or at least 20 times higher or at least 50 times higher or, preferably, at least $10^2$ higher or at least $10^3$ higher or at least $10^4$ higher affinity.

2. In an embodiment the compound is a S1R agonist the effect of which can be selectively antagonized with a specific S1R antagonist, e.g. NE-100.

3. In an embodiment of the invention the S1R agonist compound is an S1R agonist compound for use as defined herein or as defined above, said S1R agonist compound having the following formula I':

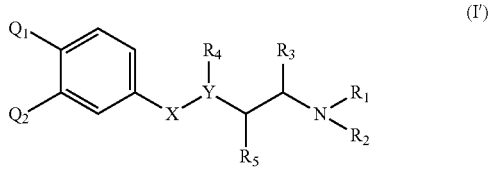

wherein
Q1 is H, halogen, pseudo-halogen, C(1-4) alkyl optionally substituted with 1, 2, 3 or 4 halogen(s), C(1-3) alkoxy, C(6-10) aryl, optionally substituted with 1, 2, 3 or 4 halogen(s),
Q2 is H, halogen, pseudo-halogen or C(1-3) alkoxy,
X is O, CH$_2$, ethylene or carbonyl (CO), amide or not present,
or X has the formula

wherein R6 is selected from the group consisting of a hydroxyl, substituted or unsubstituted C(1-6) alkyl, preferably C(1-3) alkyl and C(1-6) alkoxy, preferably C(1-3) alkoxy, C(1-2) alkoxy C(1-6) alkyl or C(1-6) alkoxyalkil, preferably C(1-4) alkoxyalkyl, C(5-10) aryl, preferably C(5-6) aryl,
or X has the formula

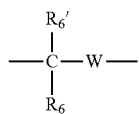

wherein W is —CH— or karbonyl (—CO—) or W is not present, and
R6 and R6' are independently substituted or unsubstituted C(1-6) alkyl preferably C(1-3) alkyl, C(1-6) alkyloxy preferably C(1-3) alkoxy, C(1-6) alkoxyalkil preferably C(1-4) alkoxyalkyl, C(1-6) alkyloxy carbonyl preferably C(1-4) alkyloxykarbonyl or at least one of R6 and R6', preferably R6' is a C(5-10) aryl preferably a C(5-6) aryl,
or R6 and R6' together form a C(4-7) cycloalkyl, preferably a cyclopentyl or a cyclohexyl
or X has the formula

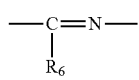

wherein R6 is selected from a substituted or unsubstituted C(1-6) alkyl preferably C(1-3) alkyl, C(1-6) alkoxy preferably C(1-3) alkoxy, C(1-6) alkoxy C(1-6) alkyl or C(1-2) alkoxy C(1-6) alkyl or C(1-6) alkoxyalkyl, or C(5-10) aryl, preferably C(5-6) aryl, Y is CH, N or O, —O—CH$_2$—CH$_2$—O— or not present wherein
if Y is O then R4 is not present,
if Y is N then R4 is H, or a C(1-3) alkyl or C(1-3) alkenyl, preferably ethyl or propenyl, or R4 and R1 together with Y, N and the carbon atoms between them form a C(5-7) heterocyclic ring,
if Y is CH then R4 is selected from a H, substituted or unsubstituted C(1-4) alkyl, C(1-4) alkoxy and C(5-10) aryl, or R4 and R1 together with Y, N and the carbon atoms between them form a C(5-7) heterocyclic ring,
R3 is selected from H, a substituted or unsubstituted C(1-6) alkyl preferably C(1-4) alkyl, C(1-6) alkoxy preferably C(1-4) alkoxy, C(1-2) alkoxy C(1-6) alkyl or C(1-6) alkoxyalkil, C(5-10) aryl, or
R3 and R6 together with the —X—Y—C2 alkyl moiety which they are attached to, may form a saturated or partially unsaturated 6 to 8 membered cycloalkyl or 6 to 8 membered heterocycloalkyl comprising 0 to 3 heteroatom(s), or
R3 and R6 together with the —X—Y—C2 alkyl moiety which they are attached to, may form a substituted or unsubstituted C(7-14) polycyclic aryl or C(7-14) polycyclic heteroaryl or C(7-14) cycloalkylaryl, or
R3 and R4 together with the —X—Y—C2 alkyl moiety which they are attached to, may form a saturated or partially unsaturated 6 to 8 membered cycloalkyl or 6 to 8 membered heterocycloalkyl comprising 0 to 3 heteroatom, or an alkylaryl, comprising preferably a substituted or unsubstituted phenyl,
R5 is C(1-3) alkyl or C(1-3) alkyloxy or
R5 and R6 together with carbon atoms which they are attached to form a 3, 4, 5 or 6 membered saturated or unsaturated, preferably saturated ring, said ring optionally comprising a heteroatom, preferably O, wherein said ring is preferably furanyl, dihidrofuranyl or tethrahydrofuranyl, wherein preferably Y is not present,
R1 and R2 are independently H or a C(1-6) alkyl, preferably methyl or ethyl,
or R1 and R2 form a 5 or 6 membered, saturated or unsaturated, preferably saturated ring,
said ring optionally comprising a heteroatom, preferably O, preferably an oxazine or morpholine, or alternatively N, preferably a diazine or piperazine ring or
said ring being optionally a substituted or unsubstituted piperidine ring, preferably a piperidine ring substituted with one or two of OH and methoxy, and phenyl, preferably a phenyl substituted with a halogen at the para position, said substituents being preferably in the para position of the piperidine ring,
or R1 is a C(2-4) alkylene preferably C(2-3) alkylene or C(3-4) alkylene and together with Y and N and the carbon atoms between Y and N form a heterocyclic ring, preferably a piperazine and R2 is a C(1-6) alkyl preferably C(1-4) alkyl, C(5-10) aryl preferably C(5-6) aryl or C(7-10) aralkyl,
or R2 is a C(2-4) alkylene preferably C(2-3) alkylene or C(3-4) alkylene and together with the N form a heterocyclic ring, preferably a tetrahydro-tetrazole,
or a pharmaceutically acceptable salt thereof.

4. In an embodiment of the invention the S1R agonist compound is an S1R agonist compound as defined herein or as defined above, said S1R agonist compound having the following formula I':

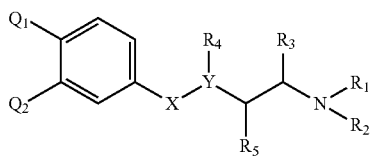 (I')

wherein

Q1 is H, halogen, pseudo-halogen, C(1-4) alkyl optionally substituted with 1, 2, 3 or 4 halogen(s), C(1-3) alkoxy, C(6-10) aryl, optionally substituted with 1, 2, 3 or 4 halogen(s), Q2 is H, halogen, pseudo-halogen or C(1-3) alkoxy, X is O, CH$_2$, ethylene or carbonyl (CO), amide or not present, or X has the formula

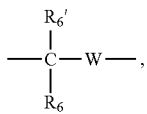

wherein

W is —CH— or karbonyl (—CO—), and

R6 and R6' are independently substituted or unsubstituted C(1-6) alkyl preferably C(1-3) alkyl, C(1-6) alkyloxy preferably C(1-3) alkoxy, C(1-6) alkoxy C(1-6) alkil preferably C(1-2) alkoxy C(1-6) alkyl, C(1-6) alkyloxy carbonyl preferably C(1-4) alkyloxykarbonyl or at least one of R6 and R6', preferably R6' is a C(5-10) aryl preferably a C(5-6) aryl, or R6 and R6' together form a C(4-7) cycloalkyl, preferably a cyclopentyl or a cyclohexyl or X has the formula

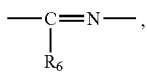

wherein

R6 is selected from a substituted or unsubstituted C(1-6) alkyl preferably C(1-3) alkyl, C(1-6) alkoxy preferably C(1-3) alkoxy, C(1-6) alkoxy C(1-6) alkyl or C(1-2) alkoxy C(1-6) alkyl or C(1-6) alkoxyalkil, C(1-6) alkyloxy carbonyl preferably C(1-4) alkyloxykarbonyl or C(5-10) aryl, preferably C(5-6) aryl, Y is CH, N or O, —O—CH$_2$—CH$_2$—O— or not present wherein if Y is O then R4 is not present, if Y is N then R4 is H, or a C(1-3) alkyl or C(1-3) alkenyl, preferably ethyl or propenyl, if Y is CH then R4 is selected from a H, substituted or unsubstituted C(1-4) alkyl, C(1-4) alkoxy and C(5-10) aryl, R3 is selected from H, a substituted or unsubstituted C(1-6) alkyl preferably C(1-4) alkyl, C(1-6) alkoxy preferably C(1-4) alkoxy, C(1-2) alkoxy C(1-6) alkyl or C(1-6) alkoxyalkil, C(5-10) aryl R5 is H, C(1-3) alkyl or C(1-3) alkyloxy R1 and R2 are independently H or a C(1-6) alkyl, preferably methyl or ethyl, or R1 and R2 form a 5 or 6 membered, saturated or unsaturated, preferably saturated ring, said ring optionally comprising a heteroatom, preferably O, preferably an oxazine or morpholine, or alternatively N, preferably a diazine or piperazine ring or said ring being optionally a substituted or unsubstituted piperidine ring, preferably a piperidine ring substituted with one or two of OH and methoxy, and phenyl, preferably a phenyl substituted with a halogen at the para position, said substituents being preferably in the para position of the piperidine ring or a pharmaceutically acceptable salt thereof.

5. In a preferred embodiment the S1R agonist compound is an S1R agonist compound as defined herein or as defined above, said S1R agonist compound having the following formula I':

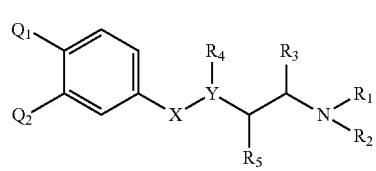 (I')

wherein

Q1 is H, halogen, pseudo-halogen, C(1-2) alkyl optionally substituted with 1, 2, 3 or 4 halogen(s), C(1-2) alkoxy, C(5-6) aryl, optionally substituted with 1, 2, 3 or 4 halogen(s), Q2 is H, halogen or pseudo-halogen, X is O, or X has the formula

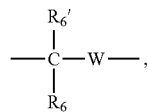

wherein

W is —CH— or karbonyl (—CO—), and

R6 and R6' are independently substituted or unsubstituted C(1-3) alkyl, C(1-3) alkoxy, preferably C(1-2) alkoxy C(1-6) alkyl, C(1-4) alkyloxykarbonyl or at least one of R6 and R6', preferably R6' is a C(5-6) aryl, or R6 and R6' together form a C(4-6) cycloalkyl, preferably a cyclopentyl or a cyclohexyl or X has the formula

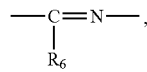

wherein

R6 is selected from C(1-3) alkyl, C(1-3) alkoxy, C(1-4) alkoxy C(1-6) alkyl or C(1-6) alkoxyalkil, C(1-4) alkyloxykarbonyl or C(5-6) aryl, Y is O or —O—CH$_2$—CH$_2$—O— wherein

R4 is not present,

R3 is selected from H, C(1-4) alkyl, C(1-4) alkoxy, C(1-2) alkoxy C(1-6) alkyl, C(1-6) alkoxyalkil, or C(5-6) aryl R5 is H, C(1-3) alkyl or C(1-3) alkyloxy
R1 and R2 are independently H or a methyl or ethyl, or
R1 and R2 form a 5 or 6 membered, saturated or unsaturated, preferably saturated ring, said ring optionally comprising a heteroatom, preferably O, preferably an oxazine or morpholine, or alternatively N, preferably a diazine or piperazine ring or
said ring being optionally a substituted or unsubstituted piperidine ring, preferably a piperidine ring substituted with one or two of OH and methoxy, and phenyl, preferably a phenyl substituted with a halogen at the para position, said substituents being preferably in the para position of the piperidine ring
or a pharmaceutically acceptable salt thereof.

6. In a further preferred embodiment said S1R agonist compound has the following formula II:

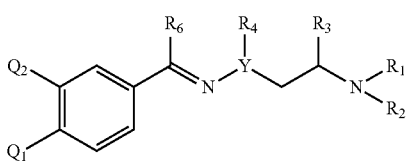

(II)

wherein
Q1 is a Cl or F or a methyl substituted with halogen selected from $CH_2F$, $CHF_2CF_3$, $CH_2Cl$, $CHCl_2$, $CCl_3$, or methoxy
Q2 is H, Cl or F,
R6 is selected from a substituted or unsubstituted C(1-3) alkyl, C(1-3) alkoxy, C(1-2) alkoxy C(1-6) alkyl, C(5-6) aryl,
Y is O
R4 is not present,
R3 is H, methyl or ethyl,
R5 is H, methyl or ethyl,
R1 and R2 are independently H, methyl or ethyl,
or a pharmaceutically acceptable salt thereof.

7. In a preferred embodiment in formula II
Q1 is a methyl substituted with halogen selected from $CHF_2$, $CF_3$, $CHCl_2$ and $CCl_3$,
Q2 is H,
R6 is selected from a substituted or unsubstituted C(1-2) alkoxy C(2-5) alkyl,
Y is O
R4 is not present,
R3 is H or methyl,
R5 is H, methyl or ethyl,
R1 and R2 are independently H, methyl or ethyl,
or a pharmaceutically acceptable salt thereof.

8. In a highly preferred embodiment the compound is fluvoxamine.

9. In a preferred embodiment said S1R agonist compound has the following formula IV

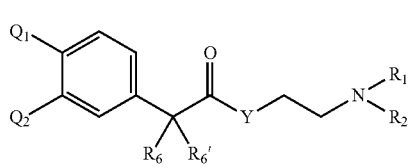

(IV)

wherein Q1 and Q2 are, independently from each other, H or C(1-2) alkyl,
R6 and R6' together form a C(4-6) cycloalkyl, preferably a cyclopentyl or a cyclohexyl
Y is O or O—$CH_2$—$CH_2$—O,
R3 is H, methyl or ethyl,
R5 is H, methyl or ethyl,
and R1 and R2 are independently H or, methyl or ethyl, or
R1 and R2 form a 5 or 6 membered ring which is saturated or unsaturated, preferably saturated,
said ring optionally comprising a heteroatom, preferably O, preferably said ring being oxazine or morpholine, or N, preferably said ring being diazine or piperazine ring.

10. In a preferred embodiment the compound is selected from PRE-084 and pentoxyverine (carbetapentane).

11. In a highly preferred embodiment the compound is PRE-084

Preferred is the ex vivo use of an S1R agonist compound for reducing, delaying or preventing cellular damage during storage of an whole or partial organ or tissue stored in a preservation solution, wherein the S1R agonist compound is fluvoxamine or PRE-084, in particular fluvoxamine, and the organ is the kidney or the liver.

Preservation solution for ex vivo storage of a transplantable whole or partial organ or tissue, said solution comprising a sigma 1 receptor (S1R) agonist compound.

Preservation solution for ex vivo storage of a transplantable whole or partial organ or tissue, said solution comprising a sigma 1 receptor (S1R) agonist compound, wherein the whole or partial organ is selected from heart, lung, abdominal organs including liver, pancreas, intestine, kidney; skin.

Preservation solution for ex vivo storage of a transplantable whole or partial organ or tissue, said solution comprising a sigma 1 receptor (S1R) agonist compound, and the solution is adapted for the preservation of the kidney and/or the liver.

An organ or tissue preservation solution for storage of a whole or partial organ or tissue, said solution comprising an S1R agonist compound. The S1R agonist compound is preferably a compound defined in numbered paragraphs 1-11. In more preferred embodiment the S1R agonist compound is fluvoxamine or PRE-084. Fluvoxamine is highly preferred. In preferred embodiments the organ is selected from heart, lung and abdominal organs including liver, pancreas, intestine, kidney; skin, eye, bone marrow. In a more preferred embodiment the organ is the kidney or the liver.

An organ or tissue preservation solution for cold storage of a transplantable whole or partial organ or tissue, said solution comprising an S1R agonist compound. A method for the preservation of an whole or partial organ or tissue, the method comprising maintaining or maintaining and perfusing the organ or tissue in a preservation solution as defined hereinabove and in the claims. In a preferred embodiment the organ or tissue is stored in the preservation solution at a temperature of from 0° C.-10° C., more preferably at a temperature of from 0° C.-4° C. and highly preferably at a temperature of about 4° C. The S1R agonist compound is preferably selected from the compounds defined in numbered paragraphs 1-11. In a preferred embodiment the S1R agonist compound is fluvoxamine or PRE-084. Fluvoxamine is highly preferred. The preservation solution may have a higher temperature (e.g. 4° C.) when used for perfusing the organ/tissue in preparation for/during isolation and a lower temperature (e.g. about 0° C.) when used for storage. In preferred embodiments the organ or tissue has been isolated from the body of a living or deceased donor subject

(A) Renal Kidney injury molecule-1 (Kim1) mRNA expression normalized to β-actin (Actb) expression in sham-operated (SHAM) rats or after 24 hours of reperfusion in vehicle-treated, autotransplanted (ATx VEH), fluvoxamine-treated, autotransplanted (ATx FLU) and SA-4503-treated (ATx SA) rats. (B) Renal Neutrophil gelatinase-associated lipocalin (Lcn2) mRNA expression normalized to β-actin expression. (C) Tubular dilatation in the kidney. (D) Representative images of tubular lumen dilatation on PAS-stained kidney sections. Red lines show tubular diameters, 200× magnification, scale bar=50 μm. +++$p<0.001$ versus SHAM; $p<0.01$ versus ATx VEH; *$p<0.001$ versus ATx VEH; n=6-8 per group.

Figure 3:
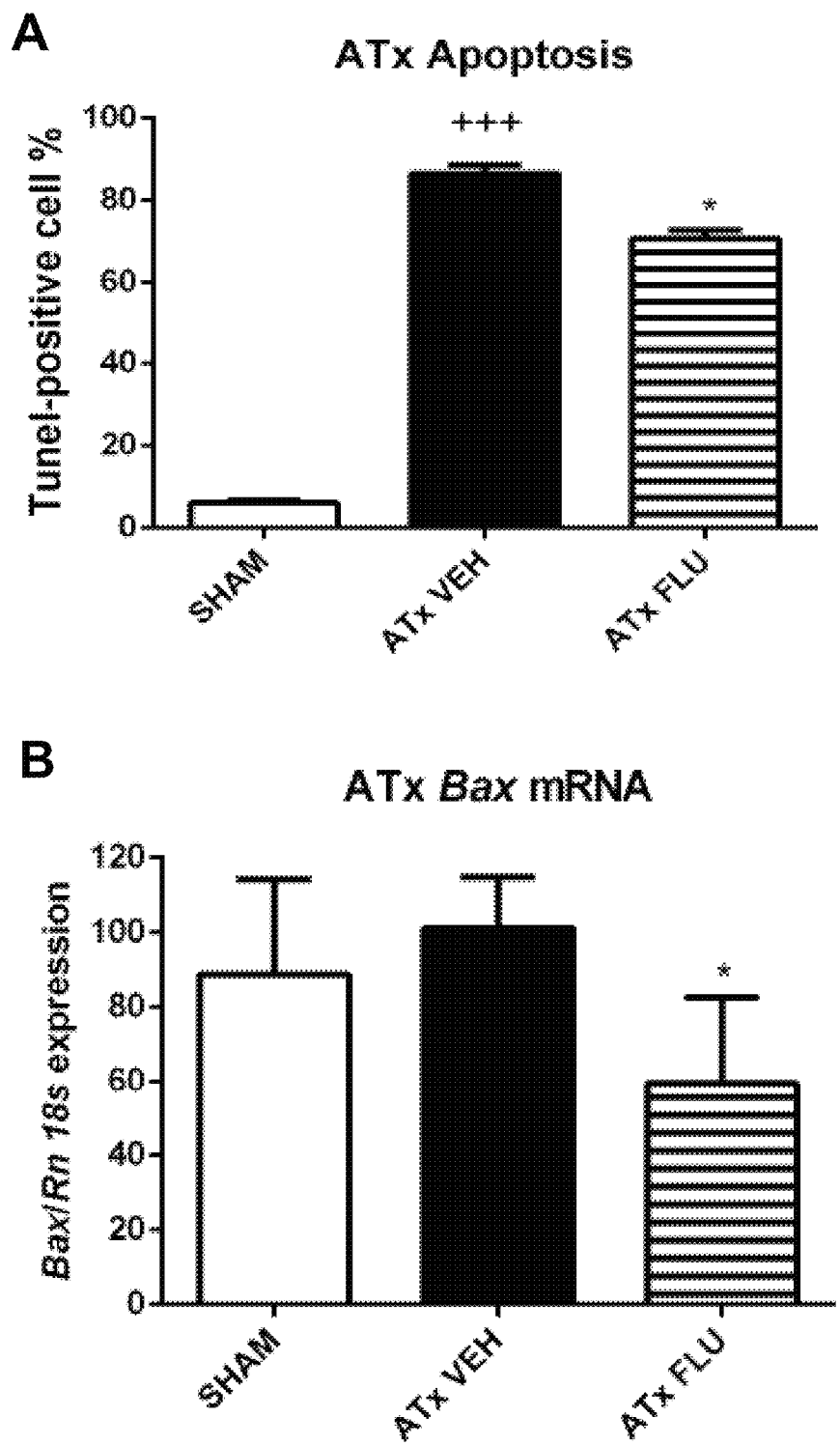
Figure 3:
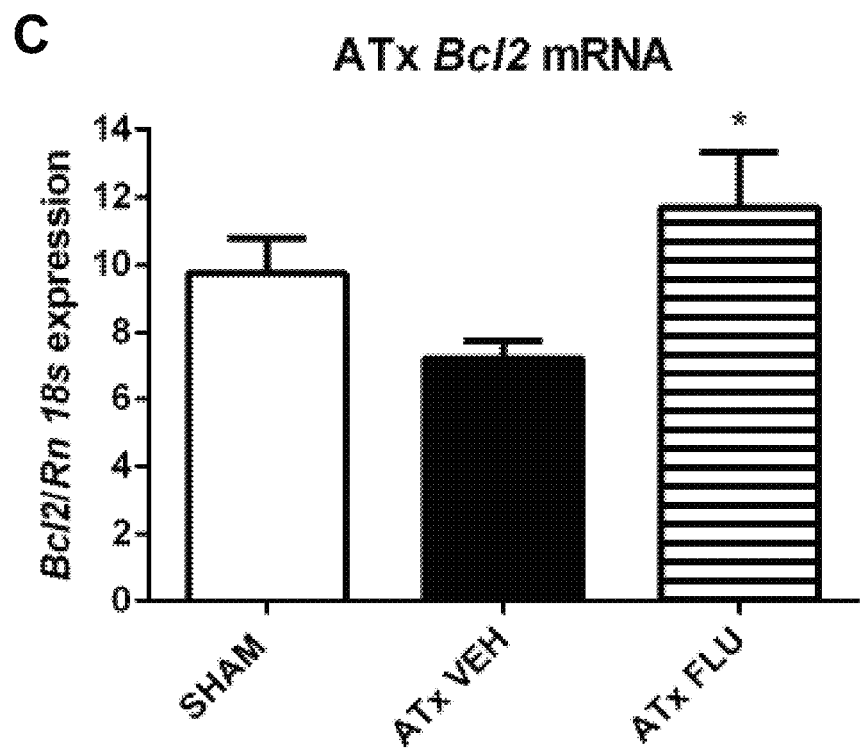
Figure 3:
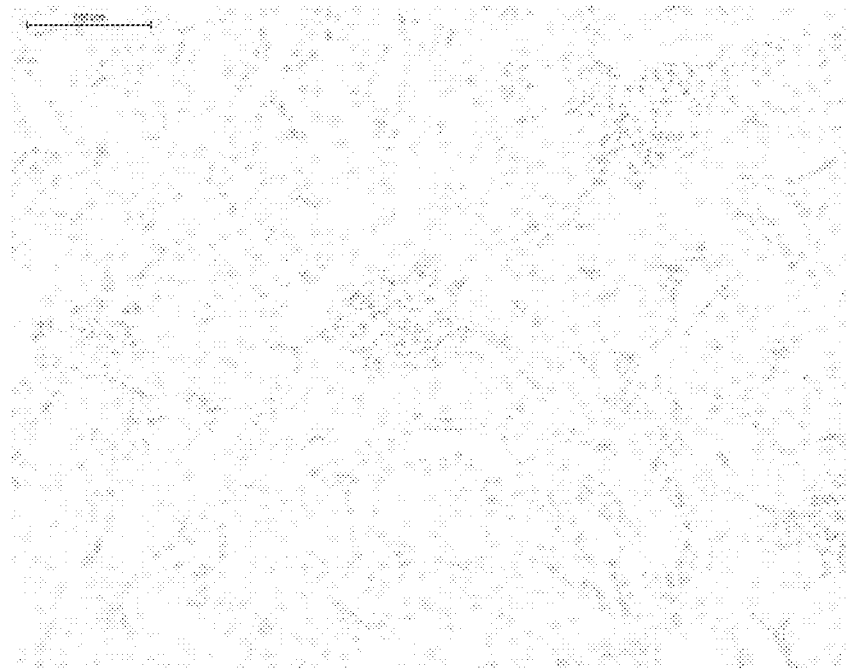
Figure 3:
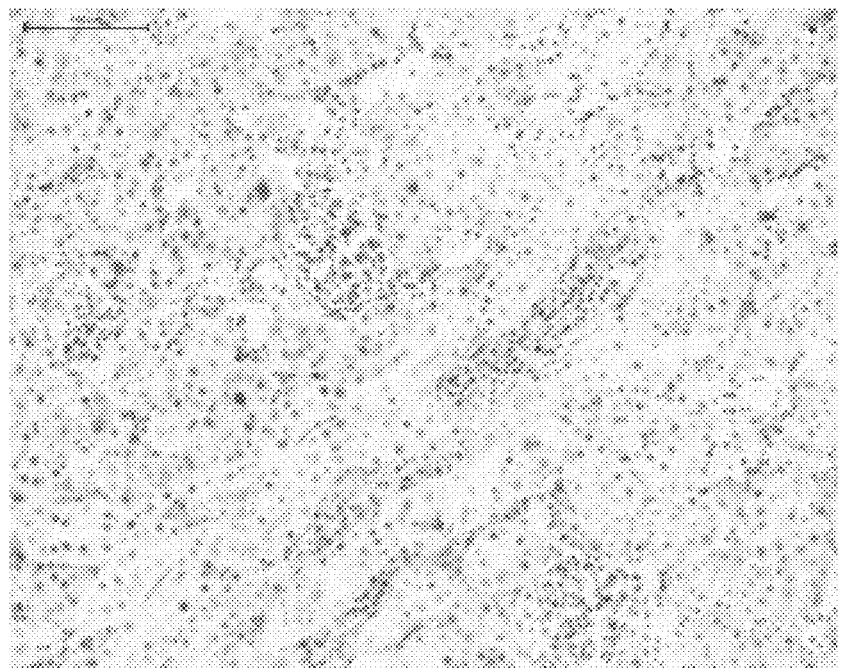
Figure 3:
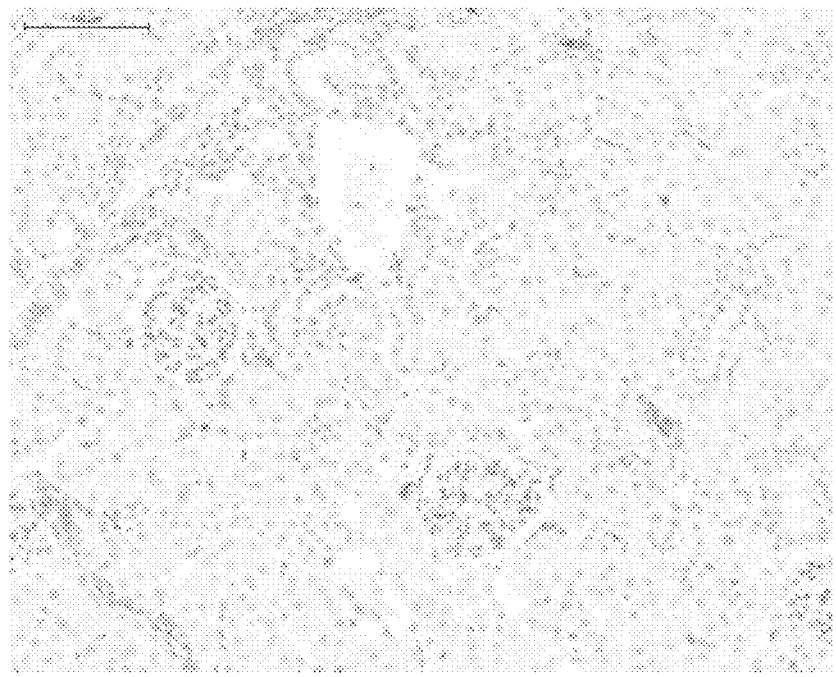

FIG. 3. S1R agonism decreases the ATx-induced apoptosis in the kidney.

(A) Ratio of Tunel-positive apoptotic cells in the kidney in sham-operated (SHAM) rats or after 24 hours of reperfusion in vehicle-treated, autotransplanted (ATx VEH), fluvoxamine-treated, autotransplanted (ATx FLU) rats. (B) Renal mRNA expression of pro-apoptotic Bax normalized to 18s ribosomal RNA (Rn 18s) expression. (C) Renal mRNA expression of anti-apoptotic Bcl2 normalized to 18s rRNA expression. (D) Representative images of Tunel-stained kidney sections. Tunel-positive brown staining of nuclei show apoptotic cells, 200× magnification, scale bar=100 μm. +++$p<0.001$ versus SHAM; *$p<0.05$ versus ATx VEH; n=6-8 per group.

Figure 4:
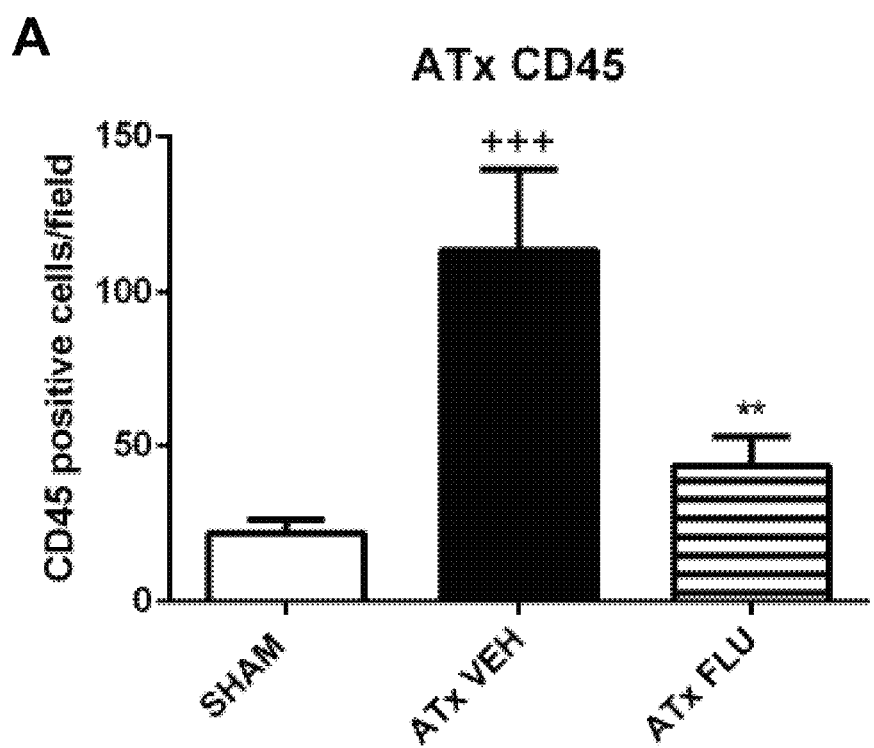
Figure 4:
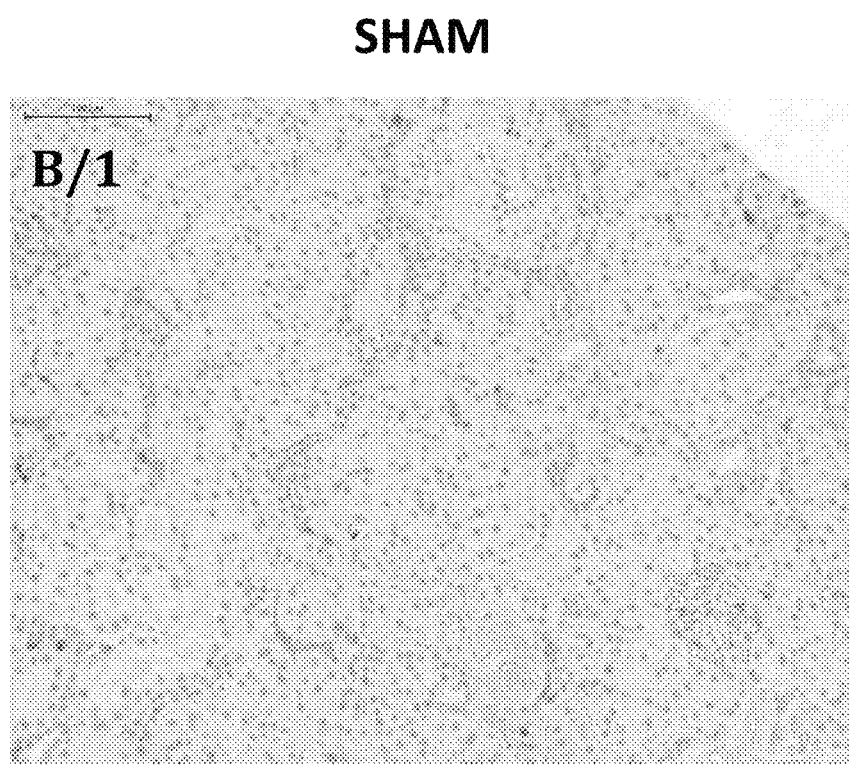
Figure 4:
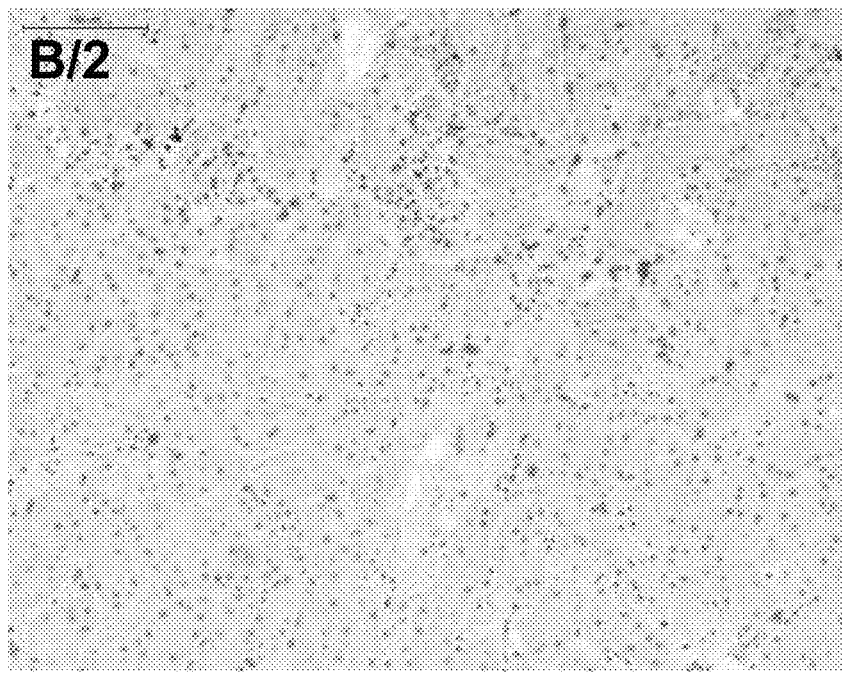
Figure 4:
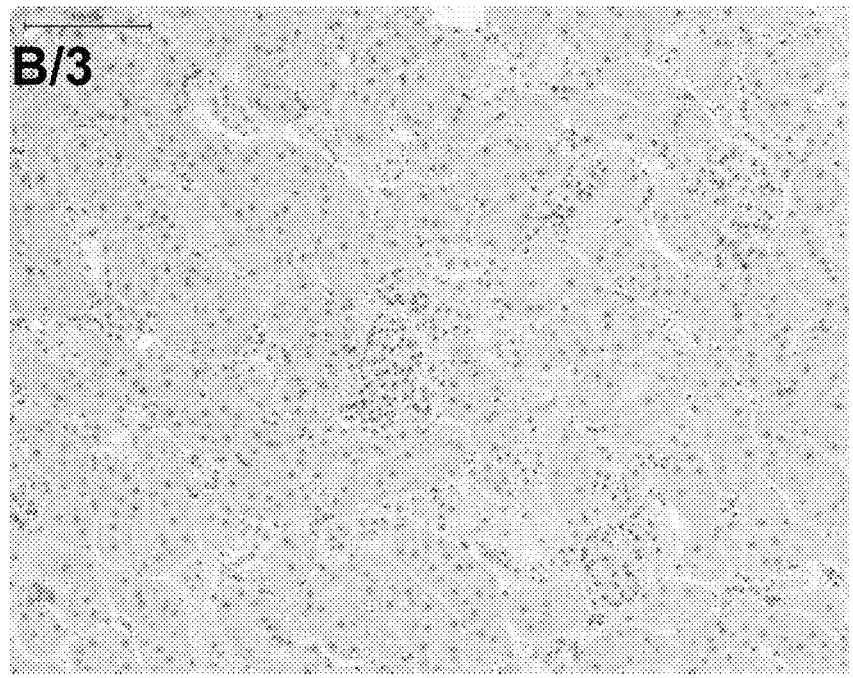

FIG. 4. Effect of S1R agonism on ATx-induced inflammatory response in the kidney.

(A) The number of CD45$^+$ lymphocytes infiltrated to the corticomedullary regions of the kidney in sham-operated (SHAM) rats or after 24 hours of reperfusion in vehicle-treated, autotransplanted (ATx VEH), fluvoxamine-treated, autotransplanted (ATx FLU) rats. (B) Representative immunohistochemical images of CD45$^+$ lymphocytes infiltrated to the corticomedullary regions. Brown staining shows CD45$^+$ lymphocytes, 200× magnification, scale bar=100 μm. +++$p<0.001$ versus SHAM; **$p<0.01$ versus ATx VEH; n=6-8 per group.

Figure 5:
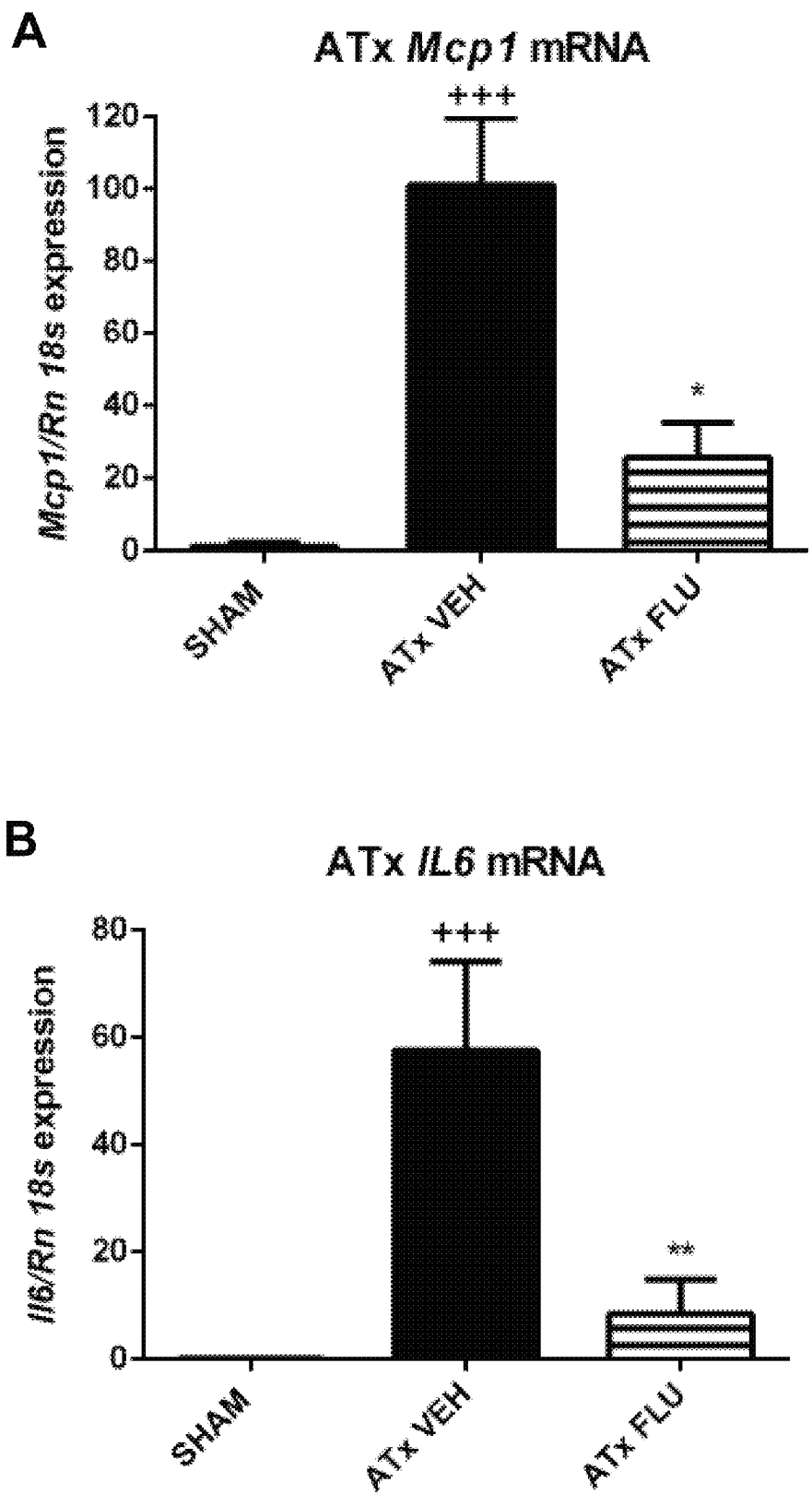
Figure 5:
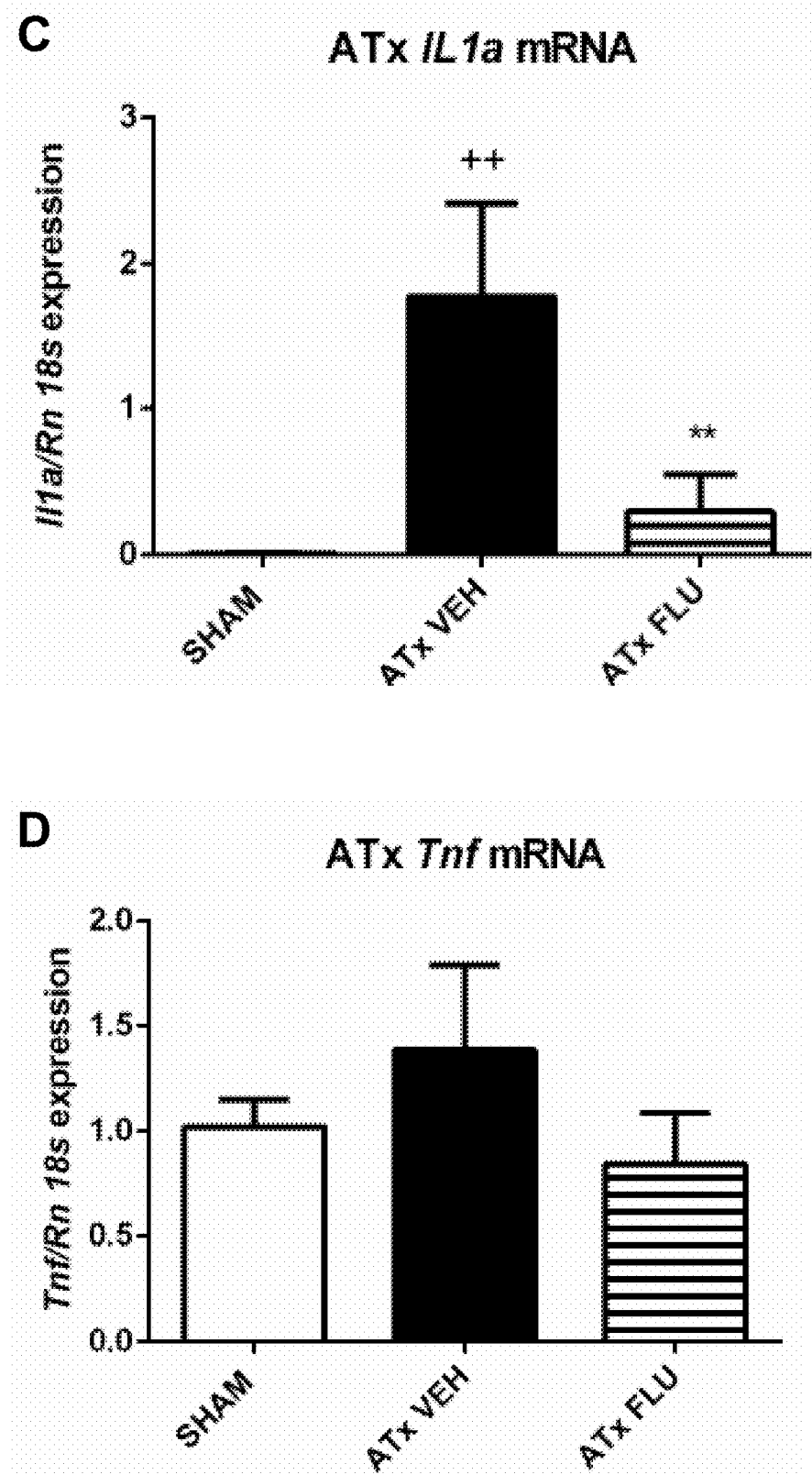
Figure 5:
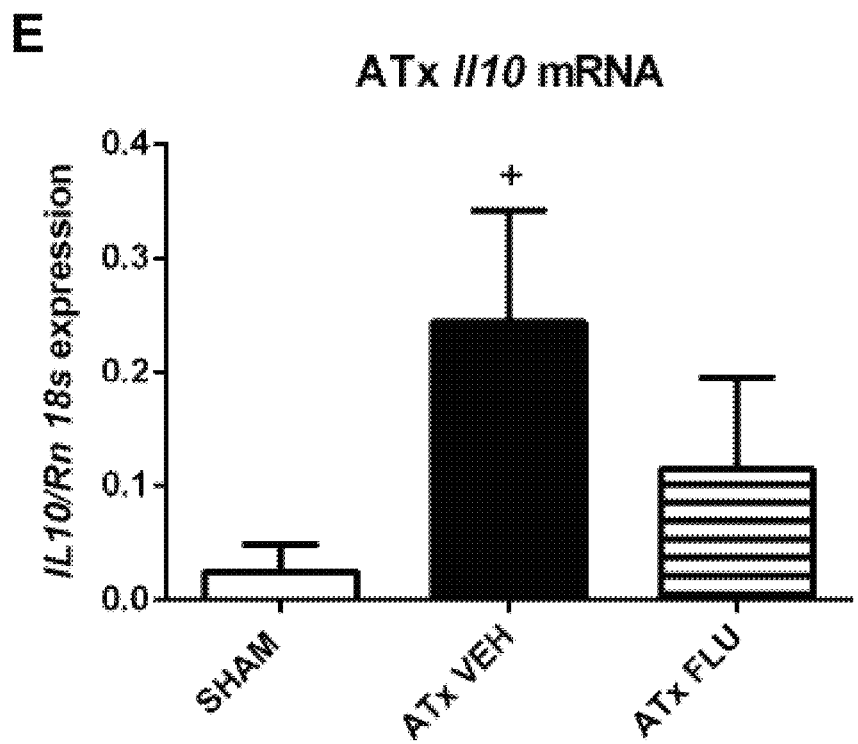
Figure 5:
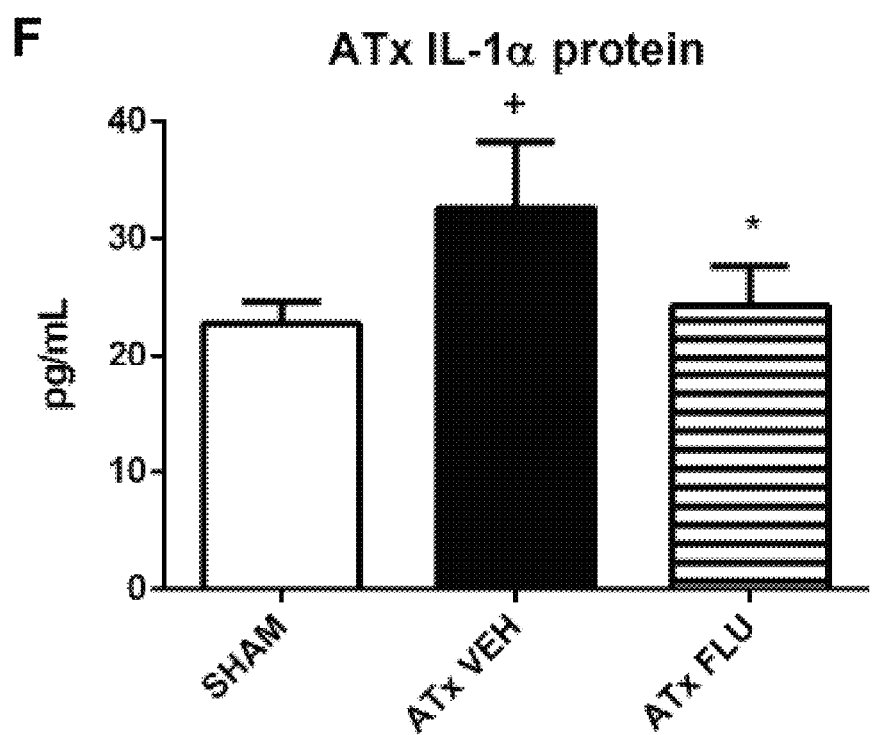
Figure 5:
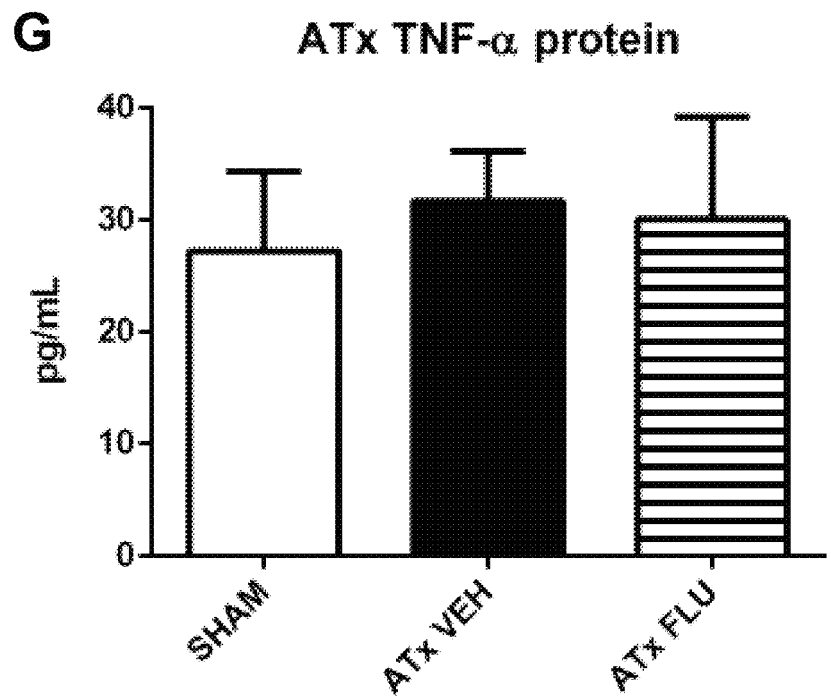
Figure 5:
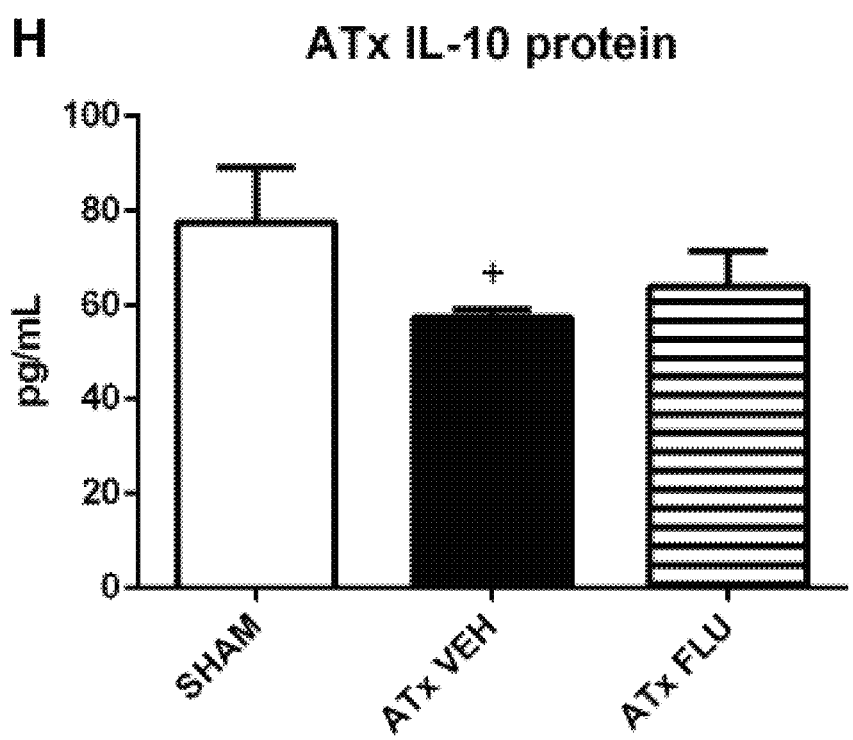

FIG. 5. Effect of S1R agonism on ATx-induced inflammatory response in the kidney.

(A) Renal Monocyte chemoattractant protein-1 (Mcp1) mRNA expression normalized to 18s rRNA expression in sham-operated (SHAM) rats or after 24 hours of reperfusion in vehicle-treated, autotransplanted (ATx VEH), fluvoxamine-treated, autotransplanted (ATx FLU) rats. (B) Renal Interleukin-6 (Il6) mRNA expression normalized to 18s rRNA expression. (C) Renal Interleukin-1α (Il1α) mRNA expression normalized to 18s rRNA expression. (D) Renal Tumor necrosis factor-α (Tnf) mRNA expression normalized to 18s rRNA expression. (E) Renal Interleukin-10 (Il10) mRNA expression normalized to 18s rRNA expression. (F) Renal protein expression of IL-1α. (G) Renal protein expression of TNF-α. (H) Renal protein expression of IL-10. +$p<0.05$ versus SHAM; ++$p<0.01$ versus SHAM; +++$p<0.001$ versus SHAM; *$p<0.05$ versus ATx VEH; **$p<0.01$ versus ATx VEH; n=6-8 per group.

Figure 6:
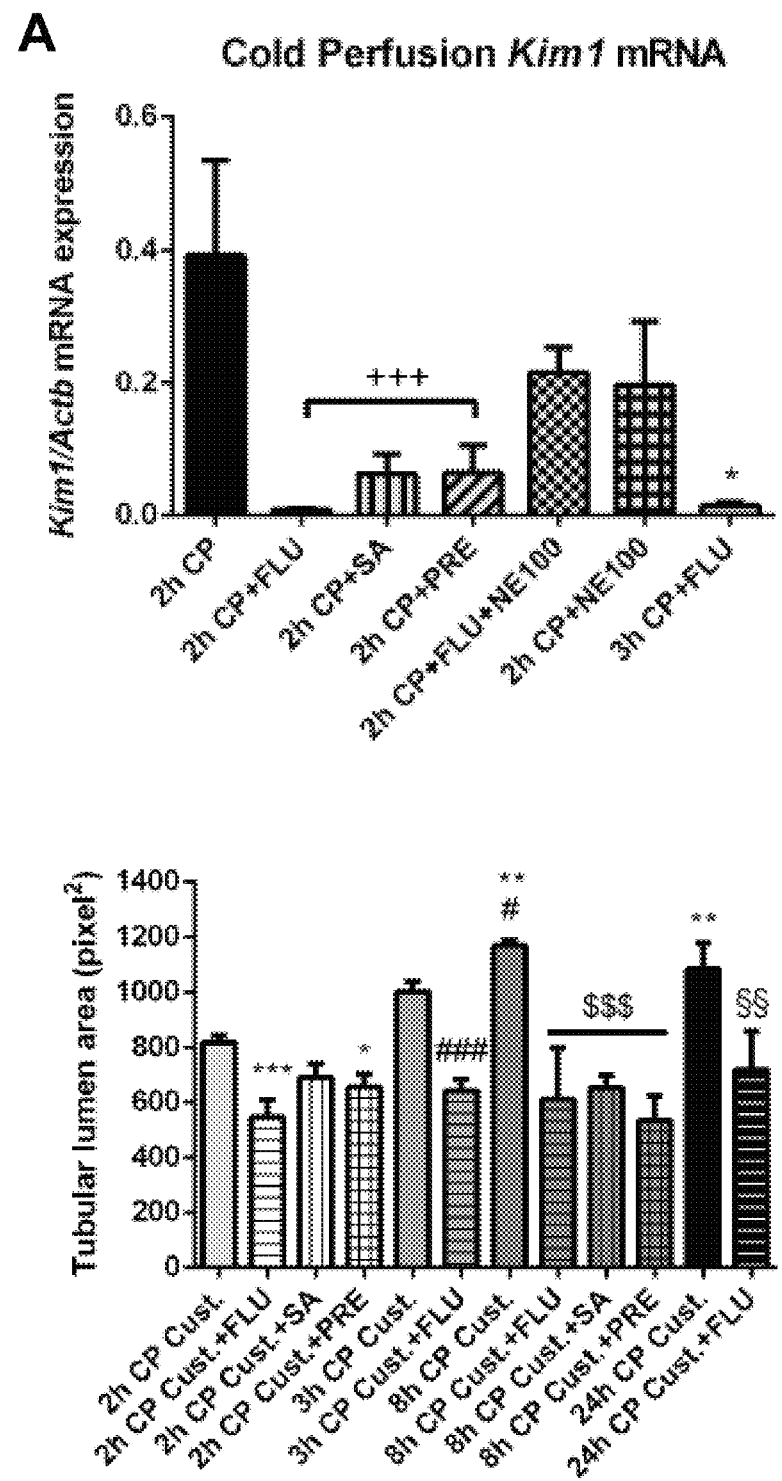

FIG. 6. Preservation solution containing S1R agonists ameliorates cold ischemia-induced tubular damage.

(A) Renal Kim1 mRNA expression normalized to 18s rRNA expression in the following groups: kidneys subjected to 2 hours of cold perfusion (2h CP); 2 hours of cold perfusion with preservation solution containing fluvoxamine (2h CP+FLU); 2 hours of cold perfusion with preservation solution containing SA-4503 (2h CP+SA); 2 hours of cold perfusion with preservation solution containing S1R agonist PRE-084 (2h CP+PRE); 2 hours of cold perfusion with preservation solution containing FLU and S1R antagonist NE100 (2h CP+FLU+NE100; 2 hours of cold perfusion with preservation solution containing NE100 (2h CP+NE100) and 3 hours of cold perfusion with preservation solution containing FLU (3h CP+FLU). +$p<0.05$ versus 2h CP; *$p<0.001$ versus 2h CP (B) Tubular dilatation in the kidney. *$p<0.05$ versus 2h CP Custodiol; $0.01$ versus 2h CP Custodiol; *$0.001$ versus 2h CP Custodiol; #$p<0.05$ versus 3h CP Custodiol; ####$p<0.001$ versus 3h CP Custodiol; $$$p<0.001$ versus 8h CP Custodiol; $$p<0.01$ versus 24h CP Custodiol; n=6 per group.

Figure 7:
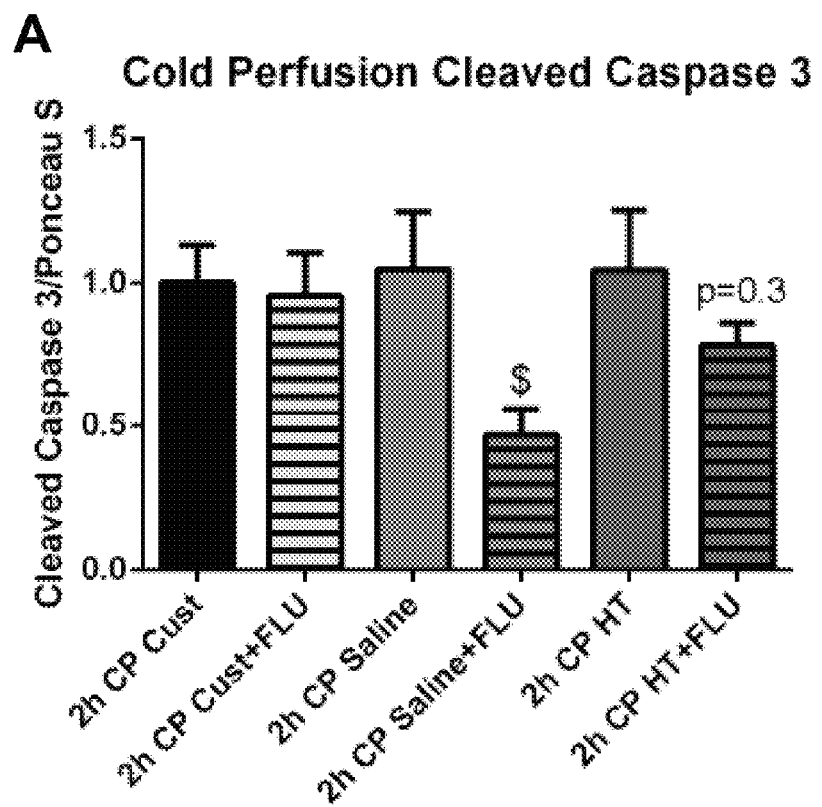
Figure 7:
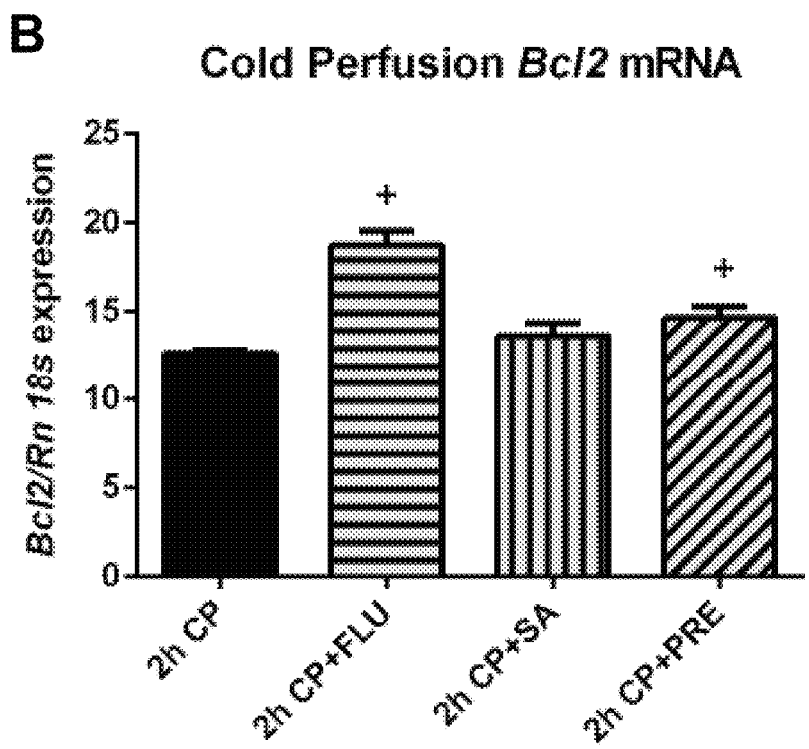

FIG. 7. Preservation solutions containing S1R agonists ameliorate cold ischemia-induced apoptosis in the kidney.

(A) Protein leves of cleaved Caspase 3 in kidneys subjected to 2 hours of cold perfusion with Custodiol solution (2h CP Cust); 2 hours of cold perfusion with Custodiol solution containing fluvoxamine (2h CP Cust+FLU); 2 hours of cold perfusion with saline (2h CP Saline); 2 hours of cold perfusion with saline containing FLU (2h CP Saline+FLU); 2 hours of cold perfusion with Hypothermosol solution (2h CP HT); 2 hours of cold perfusion with HT solution containing FLU (2h CP HT+FLU). (B) Renal anti-apoptotic Bcl2 mRNA expression normalized to 18s rRNA expression. +$p<0.05$ versus 2h CP; $$p<0.05$ versus 2h CP Saline, n=6 per group.

Figure 8:
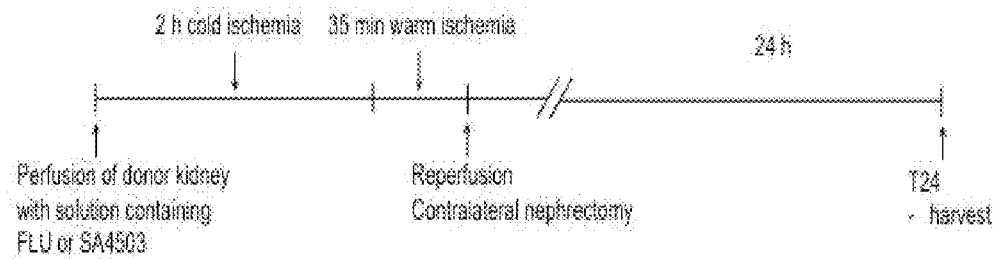

FIG. 8. Experimental design of renal autotransplantation

Figure 9:
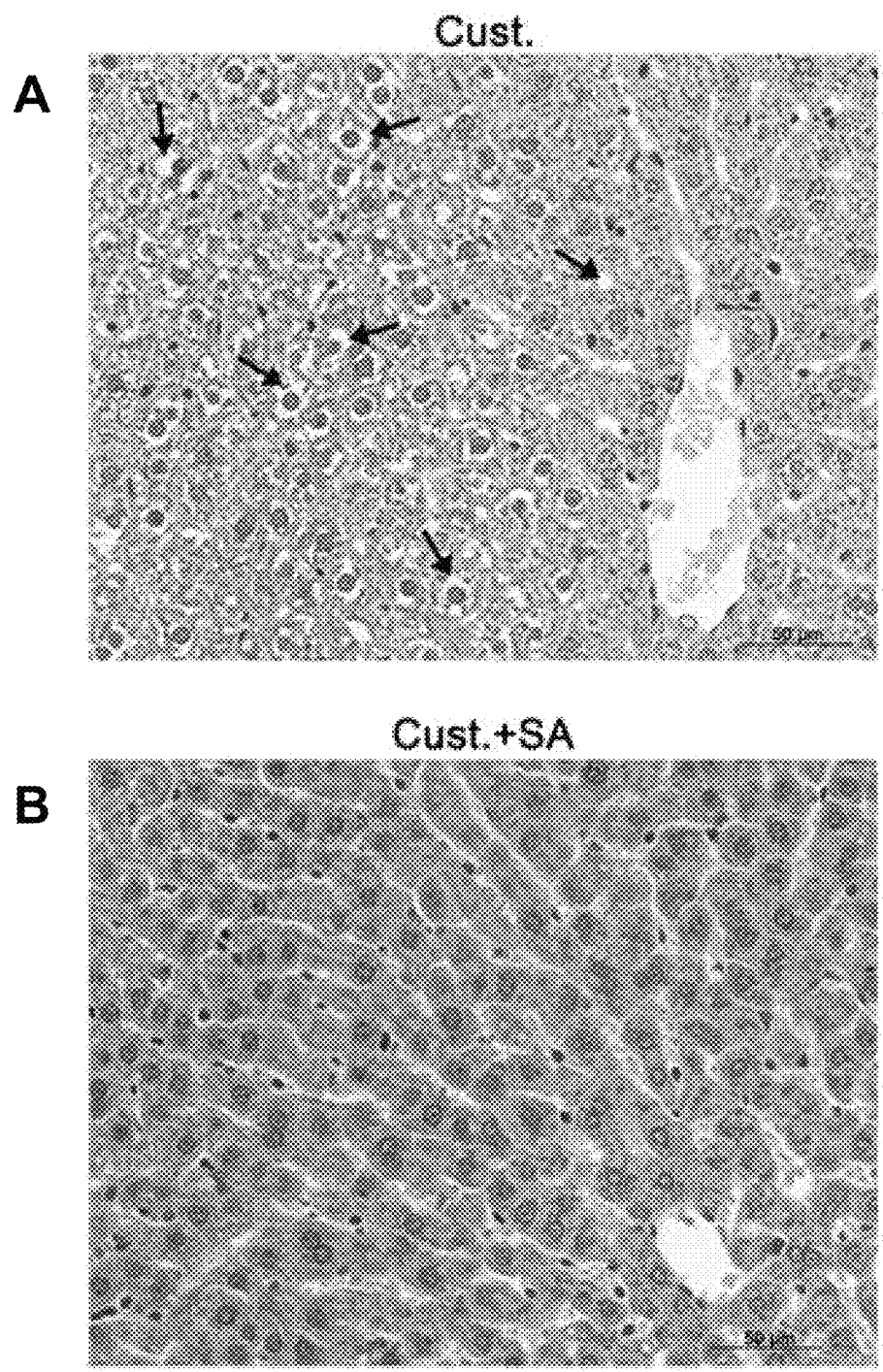
Figure 9:
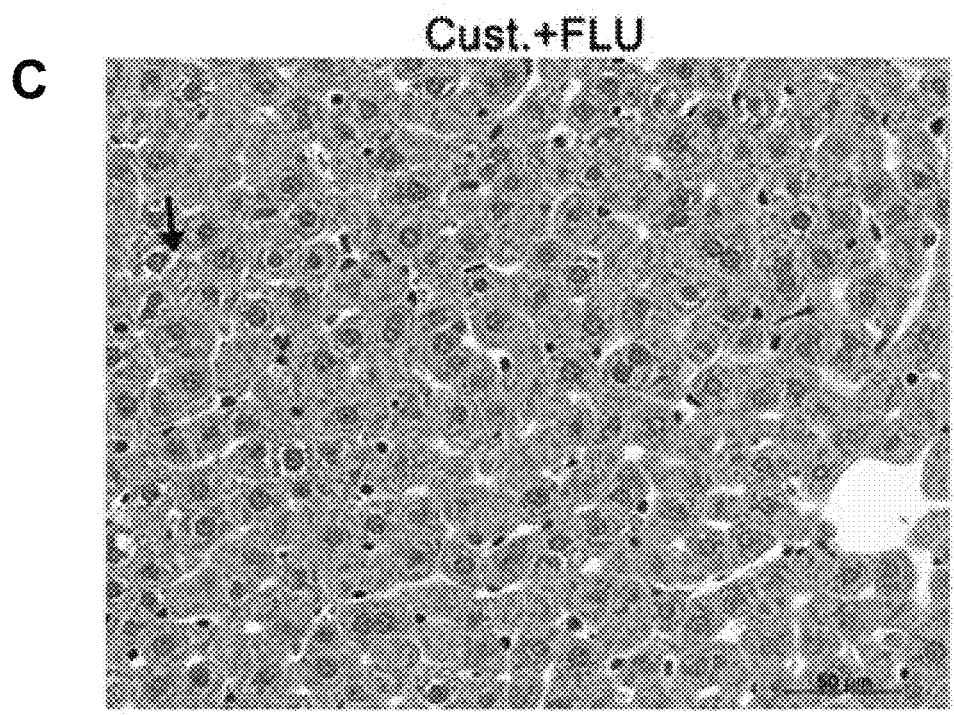
Figure 9:
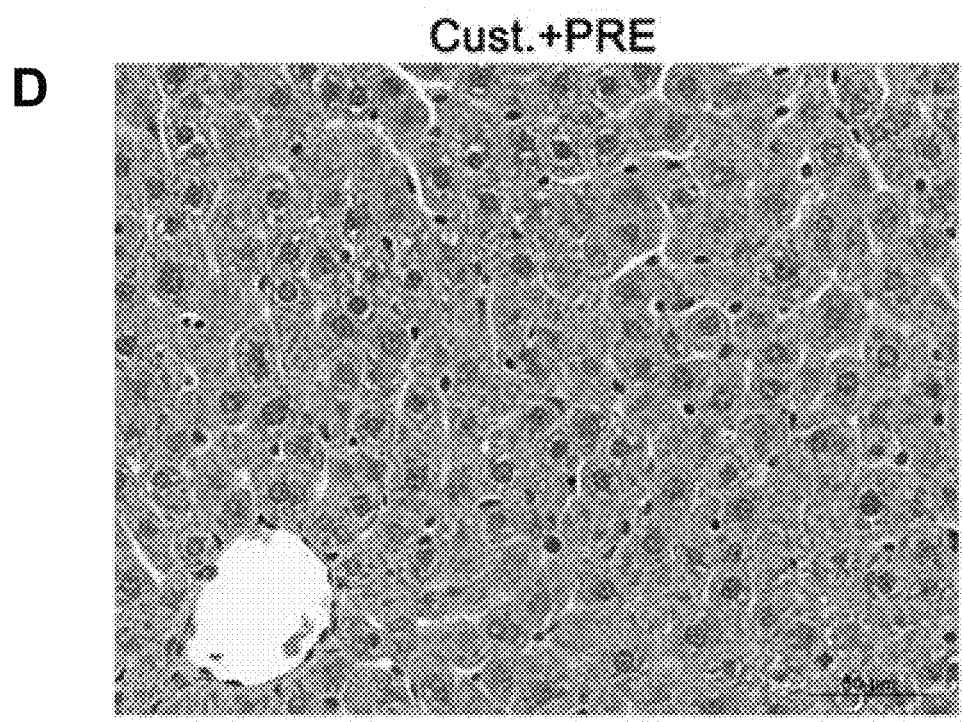

FIG. 9. HE stained liver sections after 8h cold ischemia. Black arrows point to cytoplasmic vacuoles. 400× magnification, scale bar=50 μm. (A) Custodiol, (B) Custodiol containing 0.003 mg/mL SA4503, (C) Custodiol containing 0.003 mg/mL FLU and (D) Custodiol containing 0.003 mg/mL PRE-084.

DETAILED DESCRIPTION OF THE INVENTION

Organ preservation is necessary in most cases of transplantation to maintain donor organ viability during recovery and until the time of transplantation. Storage is characterized by oxidative stress, decreased NO levels and resulting vasoconstriction, increased tendency for platelet aggregation, monocyte adhesion, leukocyte activation, edema, membrane degradation and ultimately, cell death in the form of necrosis and apoptosis. Apoptosis is found to be a significant limiting factor of storage, especially cold storage time. Apoptosis includes distinct morphologic changes as blebbing, cell shrinkage, nuclear fragmentation, chromatin condensation, chromosomal DNA fragmentation, and global mRNA decay. pH regulation is disturbed and the generation of oxygen derived free radicals is increased, which in turn impairs both cellular and systemic defense mechanisms. It is recognized that cooling increases even more the susceptibility of cells already damaged by warm ischemia to produce free radicals and attenuates the natural defense mechanisms by which cells normally deal with the low level free radical production in metabolism.

The thermal shock of isolation from the circulation and subsequent cold storage induces stress proteins. Cold storage has been shown to increase caspase-3 protein, caspase-3 activity and tubular cell apoptosis in the kidney (Jani et al. Caspase Inhibition Prevents the Increase in Caspase-3, -2, -8 and -9 Activity and Apoptosis in the Cold Ischemic Mouse Kidney Am J Transplant 4 (8) 1246-1254, 2004), while warm ischemia before cold preservation increases caspase-1 activity (Jani et al. Perfusion storage reduces apoptosis in a porcine kidney model of donation after cardiac death. Transplantation. 2011 Jan. 27; 91(2):169-75.).

Preservation enhances inflammatory responses already present during warm ischemia.

Organs from expanded criteria donors are even more susceptible to preservation and ischemia. Around 80% of transplants are from deceased donors, where cold ischemia time is a more significant risk factor for delayed graft function. The duration of cold storage therefore should be kept at a minimum.

In human transplantation, organs are usually perfused with a cold (e.g. 4° C.) preservation solution and stored and transported on ice, i.e. flushed and stored (submerged) in a preservation solution of a temperature of 0-10° C., 4-10° C. or 2-10° C. or at 4° C. Isolated organs are immersed in the cold solution and placed in a sterile bag or container which is kept cooled by stored on ice.

It was an object of the present invention to provide means to prolong preservation time, reduce organ damage, apoptosis, cellular stress and inflammatory damage caused by preservation and storage. In particular, cold storage time is prolonged and cold storage induced damages are delayed or reduced by the solutions provided herein.

"Maximum preservation time" (or "maximum storage time") refers to the period during which an organ remains viable and suitable for transplantation. This period has to be determined taking into consideration the type of organ, the method of preservation, the condition of the organ. The skilled person working in the field of organ transplantation knows the guidelines and methods to determine viability and acceptability of risks of transplantation of an organ. Although preservation time may be determined on a case by case basis, it may be predicted and calculated based on data available on the type of organ, the method of preservation, condition of the donor, etc ("predicted preservation time"). Graft assessment performed before transplantation provides reliable data on the condition of the stored organ. (In the case of the kidney, renal and tubular cell function [e.g. creatinine clearance, acid-base balance, filtration fraction, total protein excretion], perfusion parameters [e.g. haemolysis, renal blood flow] and change in kidney weight, analysis of the perfusate measuring intracellular enzymes or biomarkers of injury [AST, ALT, LDH, apoptotic markers] may be assessed.

In the context of the present disclosure "transplantable organ" or "transplantable tissue" refers to organs or tissues, respectively, which may be kept viable after isolation from a donor and may be transplanted to a recipient, where said organ or tissue remains functional. Transpantable organ or tissue may refer to artificial organs or tissues, which when transplanted into a recipient become and remain functional. Examples of transplantable organs are: kidney, heart, pancreas, liver, intestine, blood vessels, skin, eyes, etc. It is also possible to improve the condition of an organ by transplanting a part of the organ ("partial organ") or a tissue instead of the whole organ. For example, a lobe of the liver or the lung, cornea, portions of the skin may be transplanted. The means of preservation provided herein may be used for the storage of tissues and cells as well, because the same principles of preservation apply. In preferred embodiments of the invention the organ is a solid organ. A "solid organ" is a transplantable organ that has a well-defined tissue consistency or structure and is not a fluid (such as blood, bone marrow, suspension of cells etc.). Such organs include e.g. the heart, kidney, liver, lungs, and pancreas.

"Storage or preservation" refers to maintaining of an organ in a preservation solution by flushing, immersing or otherwise treating said organ with said preservation fluid. Storage encompasses both static storage and continuous (machine) perfusion. Storage or preservation refers to ex vivo storage or preservation, that is, treatment with an S1R compound or an S1R compound containing preservation solution is performed ex vivo. The ex vivo use of an S1R agonist compound is provided, i.e. said compound is contacted with the organ to be stored outside of a living body or a cadaver donor body.

"Cold storage or cold preservation" refers to storage or preservation temperatures below or at least 5° C. below or at least 10° C. below normal core temperature characteristic of the species the organ or tissue belongs to, and in particular to temperatures below 10° C.

"Cold ischemia" refers to ischemic conditions, wherein the organ is separated from the circulation. Cold ischemia therefore may refer to normothermic or subnormothermic conditions.

A "preservation solution" is to be understood as an aqueous solution suitable to keep an isolated or artificial organ or tissue viable until said organ or tissue is transplanted into a recipient. The term also refers to perfusion fluids used to perfuse the organ or tissue in preparation of isolation or storage.

"Ameliorated" as used herein refers to the prevention or delay of structural or functional damage caused by storage. It may also refer the partial or full restoration of a structure or a function affected by storage induced damage. Amelioration may be measured by assaying the marker(s) of the damage in a sample to which an agent has been administered to ameliorate the damage ("ameliorated sample") and comparing the results to predicted or measured marker(s) of damage in a sample caused by the same conditions in lack of an agent that is administered to ameliorate the damage ("non-ameliorated sample"). Amelioration may mean a statistically significant difference between the measured parameters of the ameliorated sample and the predicted or measured parameters of the non-ameliorated sample.

An "altered level" of a (bio)marker is a level of said biomarker that is—due to the damage caused by storage—different from the healthy, normal levels of said biomarker when not subjected to storage. Healthy (normal, standard) levels of a marker may be determined according to well-known guidelines and usual laboratory practice.

S1R Agonist Compounds

It is contemplated that in principle any S1R receptor agonists might be applicable in the present invention. Preferred are S1R agonists which are highly selective over S2R. Also preferred are S1R agonists which have a strong affinity to S1R receptor and which have less side-effects.

A compound is selective for S1R over S2R if it has a higher affinity for S1R than S2R, preferably 5 times higher or 20 times higher or 50 times higher or at least $10^2$ higher, at least $10^3$ higher or at least $10^4$ higher.

S1R agonists belong to various structural groups of compounds. In the present invention compounds as defined in the brief description of the invention are preferred.

In the experimental part illustrative experiments are shown with three S1R agonist compounds: fluvoxamine, SA-4503 (cumetasine) and PRE-84. Fluvoxamine was found to be the most successful of the three compounds for reducing, delaying or preventing functional and/or structural damage of an organ or tissue to be transplanted stored in a preservation solution. Compounds of formula I' are preferred. Compounds of formula II are highly preferred. Indeed, fluvoxamine has been found surprisingly more effective than SA 4503. Fluvoxamine and PRE-084 are particularly preferred. Fluvoxamine is highly preferred.

The S1R agonist compound may have the following formula I,

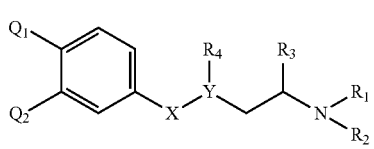
(I)

and the substituents as defined in numbered paragraph 3 above,
preferably
Q1 is halogen, pseudo-halogen, methyl-halogen or ethyl-halogen,
Q2 is H, halogen or pseudo-halogen,
X is O, $CH_2$, or X has the formula

wherein R6 is selected from the group consisting of a substituted or unsubstituted C(1-6) alkyl preferably C(1-4) alkyl, C(1-6) alkyloxy preferably C(1-4) alkyloxy, C(1-6) alkoxyalkil, C(5-10) aryl preferably C(5-6) aryl,
or X has the formula

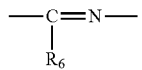

wherein is R6 selected from a substituted or unsubstituted C(1-6) alkyl preferably C(1-4 alkyl), C(1-6) alkyloxy preferably C(1-4) alkyloxy, C(1-6) alkoxyalkyl, C(5-10) aryl preferably C(5-6) alkyl,
Y is CH, N or O, wherein
if Y is O then R4 is not present,
if Y is N then R4 is H, methyl or ethyl,
if Y is CH then R4 is selected from a substituted or unsubstituted C(1-4) alkyl, C(1-4) alkyloxy, C(5-10) aryl preferably C(5-6) aryl,
R3 is selected from H, a substituted or unsubstituted C(1-6) alkyl preferably C(1-4) alkyl, C(1-6) alkyloxy preferably C(1-4) alkyloxy, C(1-6) alkoxyalkyl, C(5-10) aryl preferably C(5-6) aryl, or
R3 and R6 together with the —X—Y—C2 alkyl moiety which they are attached to, may form a saturated or partially unsaturated 6 to 8 membered cycloalkyl or 6 to 8 membered heterocycloalkyl comprising 0 to 3 heteroatom, or
R3 and R6 together with the —X—Y—C2 alkyl moiety which they are attached to, may form a substituted or unsubstituted C(7-14) polycyclic aryl or polycyclic heteroaryl, or
R3 and R4 together with the —X—Y—C2 alkyl moiety which they are attached to, may form a saturated or partially unsaturated 6 to 8 membered cycloalkyl or 6 to 8 membered heterocycloalkyl comprising 0 to 3 heteroatom, or an alkylaryl, comprising preferably a substituted or unsubstituted phenyl,
R1 and R2 are independently H, methyl or ethyl,
or a pharmaceutically acceptable salt thereof.

The S1R agonist compound may have the following formula II:

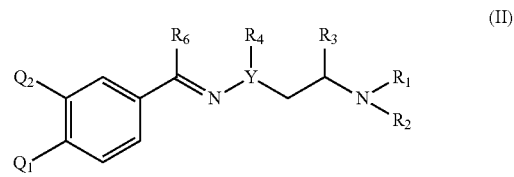
(II)

wherein
Q1 is a Cl or F or a methyl-halogen selected from $CH_2F$, $CHF_2CF_3$, $CH_2Cl$, $CHCl_2$, $CCl_3$, or optionally a methoxy
Q2 is H, Cl or F,
R6 is selected from a substituted or unsubstituted C(1-6) alkyl preferably C(1-4) alkyl, C(1-6) alkoxy preferably C(1-4) alkoxy, C(1-6) alkoxyalkyl (or C(1-6) dialkyl-ether), C(5-10) aryl preferably C(5-6) aryl,
Y is CH or O, wherein
if Y is O then R4 is not present,
if Y is CH then R4 is H, methyl or ethyl,
R3 is H, methyl or ethyl, or R3 and R4 together with the —Y—C2 alkyl moiety which they are attached to, may form a saturated or partially unsaturated cyclic group comprising 0 to 2 heteroatom(s), or R4 and R3 together form a C2-4 alkyl bridge,
R1 and R2 are independently H, methyl or ethyl,
or a pharmaceutically acceptable salt thereof.
In certain embodiments in formula II
Q1 is a methyl-halogen selected from $CHF_2$, $CF_3$, $CHCl_2$ and $CCl_3$,
Q2 is H,
X has the formula

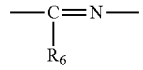

wherein R6 is selected from a substituted or unsubstituted C(1-6) alkoxyalkyl (or C(1-6) dialkyl-ether) or C(1-2) alkoxy C(2-5) alkyl,
Y is CH or O, wherein
if Y is O then R4 is not present,
if Y is CH then R4 is H, methyl or ethyl,
R3 is H or methyl,
R1 and R2 are independently H, methyl or ethyl,
or a pharmaceutically acceptable salt thereof.

A S1R agonist compound may have the following formula I"

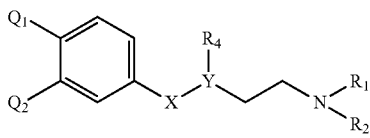

(I")

wherein Q1 and Q2 are independently from each other selected from the group consisting of a halogen, preferably I, Cl and F, and a C(1-3) alkoxy, preferably a methoxy,
Y is —CH— or N,
X is ethylene or amide,
or X has the formula

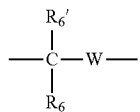

wherein W is —CH— or karbonyl (—CO—), and
R6 and R6' are independently substituted or unsubstituted C(1-3) alkyl, C(1-3) alkoxy, or one of R6 and R6' is phenyl,
R4 is C(2-3) alkyl or R4 is C(2-3) alkylene or C(2-4) alkenyl,
R1 and R2 form a 5 or 6 membered ring which is saturated or unsaturated, preferably saturated,
  said ring optionally comprising a heteroatom, preferably
    O, preferably said ring being oxazine or morpholine, or
    N, preferably said ring being diazine or piperazine ring
R1 is a C(2-3) alkylene and together with R4, Y and N and the carbon atoms between Y and N form a heterocyclic ring, preferably a piperazine or piperidine; and
R2 is a C(1-6) alkyl, C(6-10) aryl or C(7-10) aralkyl,
or R2 is a C(3-6) alkylene and together with the N form a heterocyclic ring, preferably a tetrahydro-tetrazole,
or R2 together with R1, R4, Y and N and the carbon atoms between Y and N form a bicyclic heterocyclic ring, preferably octahydropyrrolo[1,2-a]pyrazine.

An embodiment of the compound according to formula I" is a compound according to formula III':

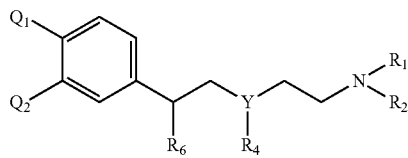

(III')

and the substituents are as defined for formula I" mutatis mutandis
wherein
R6 is C(1-3) alkyl, C(1-3) alkoxy, or R6 is phenyl.

A S1R agonist compound may have the following formula (III)

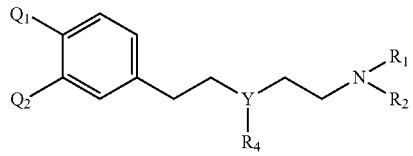

(III)

Q1 and Q2 are independently from each other selected from the group consisting of I, Cl and F, C(1-3) alkoxy, preferably a methoxy,
Y is N,
R4 is C(2-3) alkyl or R4 is C(2-3) alkylene or C(2-4) alkenyl
R1 and R2 form a 5 or 6 membered ring which is saturated or unsaturated, preferably saturated,
  said ring optionally comprising a heteroatom, preferably
    O, preferably said ring being oxazine or morpholine, or
    N, preferably said ring being diazine or piperazine ring
or R1 is a C(2-3) alkylene and together with R4, Y and N and the carbon atoms between Y and N form a heterocyclic ring, preferably a piperazine or piperidine; and
R2 is a C(1-6) alkyl, C(6-10) aryl or C(7-10) aralkyl,
or R2 is a C(3-6) alkylene and together with the N form a heterocyclic ring, preferably a tetrahydro-tetrazole,
or R2 together with R1, R4, Y and N and the carbon atoms between Y and N form a bicyclic heterocyclic ring, preferably octahydropyrrolo[1,2-a]pyrazine.
In certain embodiments of formula III
Q1 and Q2 are independently from each other selected from the group consisting of Cl, F and a methoxy,
Y is N,
R4 is C(2-3) alkyl or R4 is C(2-3) alkylene or C(2-4) alkenyl
R1 and R2 form a 5 membered ring said ring comprising a N,
or R1 is a C(2-3) alkylene and together with R4, Y and N and the carbon atoms between Y and N form a heterocyclic ring, preferably a piperazine or piperidine; and
R2 is a C(1-6) alkyl, C(6-10) aryl or C(7-10) aralkyl,
An embodiment of a compound of formula III is SA 4503 (cutamesine).

The S1R agonist compound may have the following formula IV

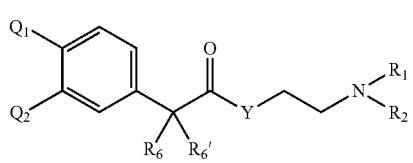

(IV)

wherein Q1 and Q2 are, independently from each other, H or C(1-2) alkyl,
R6 and R6' together form a C(4-7) cycloalkyl, preferably a cyclopentyl or a cyclohexyl
Y is O or O—CH$_2$—CH$_2$—O or NH,
and R1 and R2 are independently H or, methyl or ethyl, or
R1 and R2 form a 5 or 6 membered ring which is saturated or unsaturated, preferably saturated, said ring optionally comprising a heteroatom, preferably O, preferably said ring being oxazine or morpholine, or N, preferably said ring being diazine or piperazine ring.

A S1R agonist compound may have the following formula V

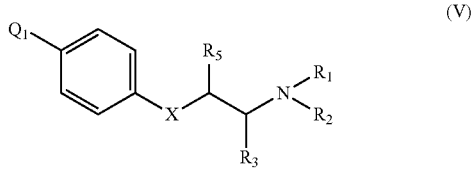

(V)

wherein Q1 is a halogen, phenyl or H,
R3 is H or Me,
R5 is H, C(1-3) methyl or C(1-3) alkoxy,
X has the formula

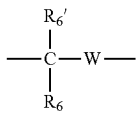

wherein W is methylene or not present, and
R6 is H or methyl
R6' is C(1-6) alkyl, C(1-6) alkyloxy or a C(6-10) aryl, preferably a phenyl,
or R5 and R6 together with the carbon atoms to which they are attached to form a 3, 4, 5 or 6 membered ring (saturated or unsaturated, preferably saturated), said ring optionally comprising a heteroatom, preferably O, wherein said ring is preferably a furanyl, dihidrofuranyl or tethrahydrofuranyl, more preferably tethrahydrofuranyl, wherein preferably the compound is Anavex 2-73,
or X has the formula

wherein R6 is selected from a substituted or unsubstituted C(1-2) alkyl and C(1-2) alkyloxy and a C(6-10) aryl, preferably C(1-2) alkyl, preferably methyl,
wherein preferably the compound is RC-33.

An S1R agonist compound may have the following formula (VI)

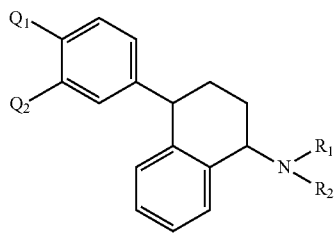

(VI)

wherein Q1 and Q2, independently from each other, are selected from the group consisting of a halogen, preferably Cl and F, and a C(1-3) alkoxy, preferably a methoxy, R1 and R2 are independently H, methyl or ethyl, In formula II Q1 and Q2 may be identical and may be selected from the group consisting of Cl and F and a methoxy, R1 and R2 are independently H, methyl or ethyl.

As used herein, the term "alkyl" alone or in combinations means a straight or branched-chain hydro-carbon group containing preferably from 1 to 6, preferably 1 to 4 or 1 to 3 carbon atom(s) or 1 to 2 carbon atom(s) (i.e. "C(1-6)" "C(1-4)" or "C(1-3)" or "C(1-2)" alkyl groups, respectively), such as methyl, ethyl, propyl, isopropyl, butyl, sec-butyl and t-butyl.

As used herein, the term "alkoxy" means an alkyl-O— group in which the alkyl group is as previously described. Non-limiting examples of suitable alkoxy groups include methoxy, ethoxy, n-propoxy, isopropoxy and n-butoxy, preferably methoxy. The bond to the parent moiety is through the oxygen (if to a carbon atom, ether oxygen).

The term "alkoxy alkyl" means an alkyl group which is substituted by an alkoxy group, i.e. an alkyl-O— group as previously described. The bond to the alkyl moiety is through the oxygen i.e. it is an ether oxygen.

An "alkenyl" as used herein, alone or in combinations, means a straight or branched-chain unsaturated hydrocarbon group containing at least one carbon-carbon double bond, said hydrocarbon group containing preferably from 2 to 6, preferably 2 to 4 or 2 to 3 or 2 carbon atom(s) (i.e. "C(2-6)" "C(2-4)" or "C(2-3)" or "C(2-2)" alkyl groups).

The term "cycloalkyl" as used herein is a non-aromatic carbon-based alkyl ring composed of at least three carbon atoms.

A "heterocyclic" ring as used herein is a cyclic moiety that has, besides carbon atom(s), atoms of at least one non-carbon element(s) as member(s) of its ring(s). Preferably the ring(s) of the heterocyclic moiety is/are 5 to 6 membered ring(s).

The term "heterocycloalkyl" refers to a "heterocyclic" ring which is derivable from cycloalkyl group as defined above, wherein at least one of the carbon atoms of the ring is replaced with a heteroatom such as, but not limited to, nitrogen or oxygen, sulphur.

The term "aryl" as used herein is a group that contains any carbon-based aromatic ring which is preferably a mono- or bicyclic group. The term aryl also includes optionally "heteroaryl" which is defined as a group that contains an aromatic group that has at least one heteroatom incorporated within the ring of the aromatic group. Examples of heteroatoms include but not limited to nitrogen and oxygen. Optionally, the term "aryl" is limited to non-heteroaryl which is also included into the term aryl and defines a group that contains an aromatic group that does not contain a heteroatom. Preferably the term "aryl" refers to a 5 or 6 membered monocyclic or 8 to 12 membered bicyclic aromatic or hteroaromatic ring. More preferably the term "aryl" refers to phenyl or naphthyl The term "aralkyl" as used herein refers to an aryl alkyl group which is linked to the parent molecule through the alkyl group, which may be further optionally substituted with one or more, preferably one to three or one to two substituents.

The term "cycloalkylaryl" refers to a group comprising a fused cycloalkyl and cycloaryl ring. Preferably the "cycloalkylaryl" moiety is attached to the compound of the invention via the cycloalkyl part of the group.

As used herein, the term "fused ring" means that the ring is fused with at least one other ring to form a group of a compound which comprises two or more rings wherein a single bond between two member atoms of the rings is, together with said two members, common in, i.e. shared by the two rings. An example of fused rings is a polycyclic aryl. A polycyclic aryl is understood herein as a group that contains multiple rings of a carbon-based group among which at least one ring is an aryl and which optionally may also comprise a cycloalkyl and/or a heterocycloalkyl.

A "substituted" moiety comprises a substituent selected from the groups and moieties as defined herein; however a substituent is smaller, i.e. shorter, i.e. consists of not more, preferably less atoms than the moiety which is/are substituted thereby.

When a moiety indicated in a formula is "not present" it means that there is a single (covalent) bond in the structure illustrated by the formula linking the atoms indicated in the vicinity of the moiety which is not present.

Although the exemplary use of an S1R agonist compound is demonstrated in a cold storage method, normothermic methods are also contemplated.

Storage of kidney grafts in a perfusion solution containing a S1R 1 receptor agonist compound exerted remarkable renoprotection marked by improved functional and histological parameters in (i) stored and (ii) stored and subsequently autotransplanted kidneys as compared to kidney grafts stored in conventional perfusion solutions without the S1R agonist compound. Healthy structure of the kidneys was also more preserved in the S1R agonist compound treated groups. As kidneys perfused with and stored in an S1R agonist compound containing perfusion solution showed significantly better functional and histological parameters than vehicle (i.e. the same perfusion solution without the S1R agonist compound) treated grafts, it is reasonably assumed that S1R agonist compound pretreated kidneys are already in a better overall condition when they are implanted into the recipient and therefore are more resistant to ischemia/reperfusion injury later during kidney transplantation.

Although most of the data presented here relates to Custodiol (Franz Kohler Chemie GMBH, Bensheim, Germany), measurements with physiological saline and HT solution (HypoThermosol® FRS preservation solution, Sigma Aldrich, St. Louis, MO, USA) indicate that the protective effect of S1R agonist compounds is not limited by the nature of the preservation solution used. In fact, a trend towards a "single" or multipurpose preservation fluid is apparent in the literature: a Scientific Registry of Transplant Recipients (SRTR) analysis from 2007 indicated that University of Wisconsin (UW) solution and Histidine Tryptophan Ketoglutarate (HTK) solution were used as the final flush solution in 63% and 28% of kidneys, respectively (2007 Annual Report of the U.S. Organ Procurement and Transplantation Network and the Scientific Registry of Transplant Recipients: Transplant Data 1997-2006. Health Resources and Services Administration, Healthcare Systems Bureau, Division of Transplantation, Rockville, MD.) Numerous studies are available comparing UW and HTK, most of them reporting similar efficacy in pancreas preservation (Becker T, Ringe B, Nyibata M, et al. Pancreas transplantation with histidine-tryptophan-ketoglutarate (HTK) solution and University of Wisconsin (UW) solution: is there a difference? *Jop*. 2007; 8(3):304-311; Potdar S, Malek S, Eghtesad B, et al. Initial experience using histidine-tryptophan-ketoglutarate solution in clinical pancreas transplantation. *Clin Transplant*. December 2004; 18(6): 661-665.) and liver transplantation (Mangus R S, Tector A J, Agarwal A, Vianna R, Murdock P, Fridell J A. Comparison of histidine-tryptophan-ketoglutarate solution (HTK) and University of Wisconsin solution (UW) in adult liver transplantation. *Liver Transpl*. February 2006; 12(2):226-230. Feng L, Zhao N, Yao X, et al. Histidine-tryptophan-ketoglutarate solution vs. University of Wisconsin solution for liver transplantation: a systematic review. *Liver Transpl*. August 2007; 13(8):1125-1136.) While all preservation fluids claim advantages over the others, each and every one of them is designed to minimize cell swelling, prevent intracellular acidosis, prevent expansion of interstitial space and prevent oxygen free radical induced injury, to preserve the intracellular milieu in the absence of effective ion pumps and to prevent necrosis. Conventional preservation solutions are not designed to specifically prevent apoptosis or inflammation.

A preservation solution may comprise osmotic active agents (e.g. citrate, lactobionate) to prevent cell swelling, electrolytes ($Na^+$, $K^+$, $Ca^{2+}$, $Mg^+$) for an osmotic effect, proton buffers (e.g. phosphate, histidine) to regulate $H^+$ concentration, a colloid (e.g. albumin, HES) for initial vascular flush and perfusion, metabolic inhibitors (e.g. allopurinol) to suppress degradation of cell constituents, metabolites (e.g. glutathione) to facilitate restoration of metabolism, free radical scavengers (e.g. vitamin E).

The composition of Custodiol and HT is given the Methods section as exemplary preservation fluids.

Given the similar composition and aim of preservation fluids, the results presented herein are indicative of the suitability of S1R agonist compounds in any preservation solutions used in preservation of transplantable isolated or artificial organs and tissues.

Cellular damage of an organ during storage is indicated by e.g. an increased number of apoptotic cells, increased expression of apoptotic marker BAX and/or cleaved caspase and/or decreased expression of anti-apoptotic marker Bcl-2. The S1R agonist compounds exerted a marked anti-apoptotic effect indicated by a decreased number of apoptotic cells as determined by TUNEL staining, decreased expression of apoptotic marker BAX, decreased level of apoptotic marker cleaved caspase (319 kDa form) and increased expression of anti-apoptotic marker Bcl-2. Thus, in an embodiment cellular damage is associated with any one or more of an increased number of apoptotic cells, increased expression of apoptotic marker BAX and cleaved caspase and decreased expression of anti-apoptotic marker Bcl-2. Reducing, delaying or preventing cellular damage during storage comprises any one or more of an decreased number of apoptotic cells, decreased expression levels of apoptotic marker BAX and decreased levels of cleaved caspase and increased expression levels of anti-apoptotic marker Bcl-2 as compared to the corresponding number of cells or expression levels, respectively, in an organ stored under identical conditions and in a preservation solution having the same composition but not comprising the S1R agonist compound. The skilled person will realize that these and other known apoptotic or anti-apoptotic markers may be measured in any transplantable organ by methods well known in the art. The presence of S1R is shown in several tissues, e.g. central nervous system, lungs, pancreas, heart, spleen, kidney, the endocrine, immune and reproductive tissues. The skilled person will also realize that S1R agonist compounds may be used in the preservation of organs which exhibit S1 receptors.

The S1R agonist compounds exerted an anti-inflammatory effect demonstrated herein by several pro-inflammatory cytokines. Markers of inflammation are well known in the art, as well as the methods to detect them. Cellular and/or functional impairment during storage is associated with the increased expression levels (as measured e.g. by mRNA levels) of any one or more of IL-6, IL-1α, TNFa and the increased number of CD45+ lymphocytes. Reducing, delaying or preventing cellular and/or functional damage therefore comprises any one or more of a decreased expression level of IL-6, decreased expression level IL-1α, decreased expression level TNFa and decreased number of CD45+ lymphocytes as compared to the corresponding number of cells or expression levels, in an organ stored under identical conditions and in a preservation solution having the same composition but not comprising the S1R agonist compound.

In an embodiment the level of one or more marker(s) selected from the number of apoptotic cells, expression level of IL-6, expression level of IL-1α is decreased as compared to the corresponding marker, in an organ stored under identical conditions and in a preservation solution having the same composition but not comprising the S1R agonist compound.

The use of an S1R agonist compound clearly prolonged preservation time in experiments described herein. Organs stored in a fluvoxamine-containing preservation solution showed 25% less tissue damage as demonstrated by histologic assay after 1.5 fold longer or even 10 fold longer preservation time than organs stored in the same preservation solution not containing fluvoxamine.

Effects of the S1R agonist compounds are exemplified by kidney transplantation and the storage of isolated kidney and liver. Functional, molecular and histological markers of kidney injury other than the ones described herein are well known in the art, as well as the methods to measure the changes of such markers.

In an embodiment the organ is the kidney or the tissue is renal tissue and functional damage is reduced, delayed or prevented, indicated by any of a decreased level of serum creatinine, decreased level of blood urea nitrogen, decreased level of blood KIM1, decreased level of blood MCP-1, decreased level of blood NGAL and increase glomerular filtration rate as compared to the corresponding marker, in an organ stored under identical conditions and in a preservation solution having the same composition but not comprising the S1R agonist compound. In another embodiment further cellular damage is reduced, delayed or prevented, as indicated by a decrease of the tubular lumen area dilatation.

Cellular damage may be assayed by measuring the level of one or more chaperones (e.g. HSP27, HSP72, HSP90), vasoactive agents (e.g. prepro-endothelin, prostacyclin, angiotensin), markers of apoptotic pathways (e.g. annexin-V, Bcl-2, caspase-3,7), markers of necrotic pathways (e.g. DNA fragmentation), markers of inflammation (e.g. TLR, NF-κβ, IL-1, IL-6, TNF-α), markers of activation of the immune system (e.g. IL-1, IL-6), markers of endoplasmatic reticulum stress (e.g. Xbp1, xanthine-oxidase, SOD), markers of oxidative stress (e.g. Xbp1, xanthine-oxidase, SOD), markers of angiogenesis (e.g VEGF, SDF), markers of remodelling (e.g. MMPs, TIMP-1, TIMP-2), markers of regeneration (e.g. MMPs, TIMP-1, TIMP-2). Altered levels of these biomarkers are indicative of cellular damage. In other organs other markers of injury may be detected. For example, in case of the liver, conventional laboratory parameters, such as elevated serum ALT (alanine aminotransferase), AST (aspartate aminotransferase), gamma-GT and LDH (lactate dehydrogenase) levels are indicative of damage. In an embodiment the organ is the liver or the tissue is liver tissue, and functional damage is reduced, delayed or prevented, indicated by any of a decreased level of serum alanine aminotransferase, decreased level of serum aspartate aminotransferase, decreased level of serum gamma-GT and decreased level of serum lactate dehydrogenase as compared to the corresponding marker, in an organ stored under identical conditions and in a preservation solution having the same composition but not comprising the S1R agonist compound. The detection of inflammatory cytokines of e.g. IL-6, TNF-α, and IFN-γ or anti-inflammatory cytokine IL-10 in liver grafts is a routine exercise, as well as the detection of Caspase-3, Bcl-2, and Bax protein expression (apoptosis markers) in hepatocytes. Histological markers such as hepatocyte swelling, increased cytoplasmic vacuolization, nuclear pyknosis, sinusoidal dilatation, and focal necrosis characteristic of liver graft injury may be measured. Functional parameters, such as bile production, transaminase levels, bilirubin levels, and prothrombin time are also indicative of the functioning of a transplanted organ.

In case of pancreas grafts insulin requirements and C peptide levels as well as amylase production may be measured. Both the exocrine and endocrine pancreas may be evaluated histologically: edema, neutrophilic infiltrate, lymphocytic infiltrate, acinar, hemorrhagic and fat necrosis, apoptosis and vascular thrombosis are characteristic of tissue damage.

Measurable functional parameters of the transplanted lung (tissue): blood gases (oxygen tension), pulmonary hemodynamics (pulmonary vascular resistance), pulmonary compliance, structural parameters: dry-to-weight ratio, light microscopy, myeloperoxidase content.

Reactive oxygen species production, oxidative damage, serum troponin I, beating score may be measurable markers of transplanted heart functions.

S1R agonist compounds fluvoxamine (Flu), SA 4503 and PRE-084 were tested together with NE100, a specific S1R antagonist, further confirming the role of S1R in the protective effect of these compounds. NE 100 antagonism has been showed in several experiments to underline the role of the S1R pathway.

Cold ischemia time in our experimental setting was set for 2 or 3 hours according to literary data and even to 24 hours and was validated by markedly impaired renal functional parameters. The temperature of the preservation solution was 4° C. for perfusion and about 0° C. during storage, as customary in the art and in human transplantation (the isolated organ is kept on ice).

The study was designed to model the most probable real life scenario of a deceased donor and thus did not involve pretreatment of the donor with the S1R agonist compound. This treatment arrangement also excluded the systemic and local anti-inflammatory effects of the S1R agonist compound known to take place in the donor and to protect the kidney against IRI before isolation thereof.

Treatment of the recipient with the S1R agonist compound was also avoided and therefore systemic protective effects of the compound could also not contribute to the improved functional and histological parameters measured.

Adding the S1R agonist compound to the preservation solution results in a situation very much different from those known from the art where either the donor or the recipient or both were treated with the test agent. In the present arrangement only the transplanted kidney is affected. Furthermore, the effects of an active agent used in the preservation solution only (i.e. ex vivo) are certainly different from those of the same agent administered systemically into a living body.

To test the functionality of the isolated and stored kidneys, we have not only analyzed the kidneys after storage, but also used the rat kidney autotransplantation model. This model allows the elimination of the confounding effects of an immune response and the toxicities related to immunosuppression to prevent allo graft rejection.

Addition of an S1R Agonist Compound to the Preservation Solution Improves Kidney Structure after (i) Cold Storage and (ii) Cold Storage and Subsequent Transplantation.

Kidney structure after (i) storage and (ii) transplantation after storage was evaluated as described in the Methods section. The degree of tubular damage was quantified by measuring tubular lumen areas. Dilatation of the tubular lumen is caused by degradation of tubular epithelial cells and is a good indicator of tubular damage.

(i) Storage. Tubular lumens were less dilated in kidneys stored in a preservation solution to which fluvoxamine was added. The addition of SA 4503 or PRE-084 also showed a similar effect, although to a lesser degree. Increasing tubular damage can be seen on FIG. 6B, showing the size of tubular lumen areas measured after 2 and 3 hours of cold storage. Addition of fluvoxamine inhibited this increase of damage. It is also apparent that structural damage in the presence of Flu is less pronounced after 3, 8 or even 24 hours of cold ischemia than after a shorter, 2 hours ischemia without Flu. This result strongly indicates that S1R agonist compounds and in particular fluvoxamine have the potential to prolong storage (cold ischemia) time.

(ii) Transplantation after storage. Tubular lumen areas measured are significantly smaller when fluvoxamine or SA 4503 is added to the preservation fluid as compared to the standard preservation solution, showing that a S1R agonist compound containing solution better preserves the structure of the isolated kidney. (FIG. 2C)

Figure 1:
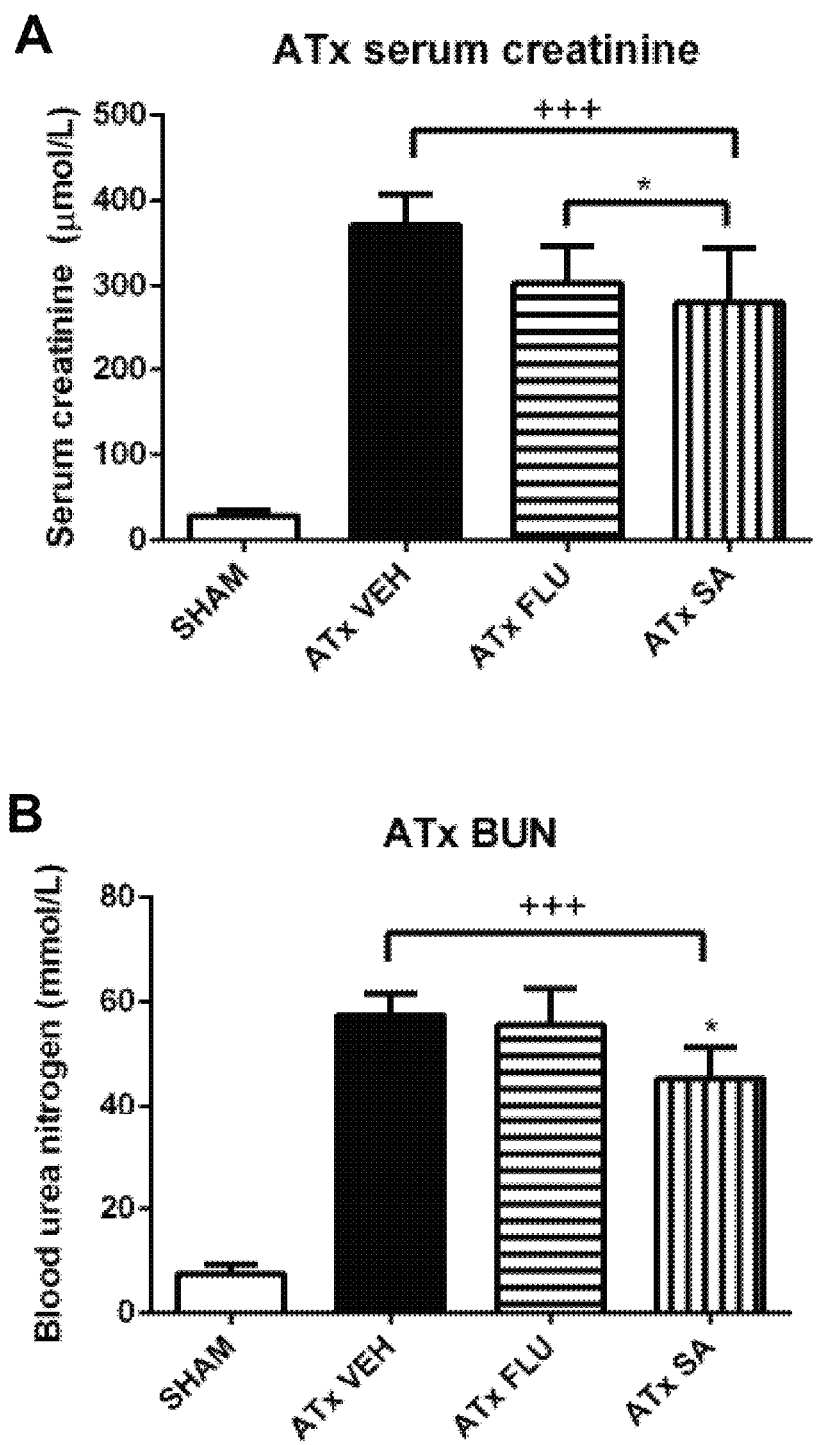
FIG. 1. Sigma-1 receptor (S1R) agonists improve renal autotransplantation (ATx)-induced renal function (A) Serum creatinine levels in sham-operated (SHAM) or after 24 hours of reperfusion in vehicle-treated, autotransplanted (ATx VEH), S1R agonist fluvoxamine-treated, autotransplanted (ATx FLU) and S1R agonist SA-4503-treated (ATx SA) rats. (B) Blood urea nitrogen (BUN) levels after 24 hours of reperfusion. (C) Serum aspartate aminotransferase (AST) levels after 24 hours of reperfusion. +++$p<0.05$ versus SHAM; *$p<0.05$ versus ATx VEH; **$p<0.01$ versus ATx VEH; n=6-8 per group.
Figure 1:
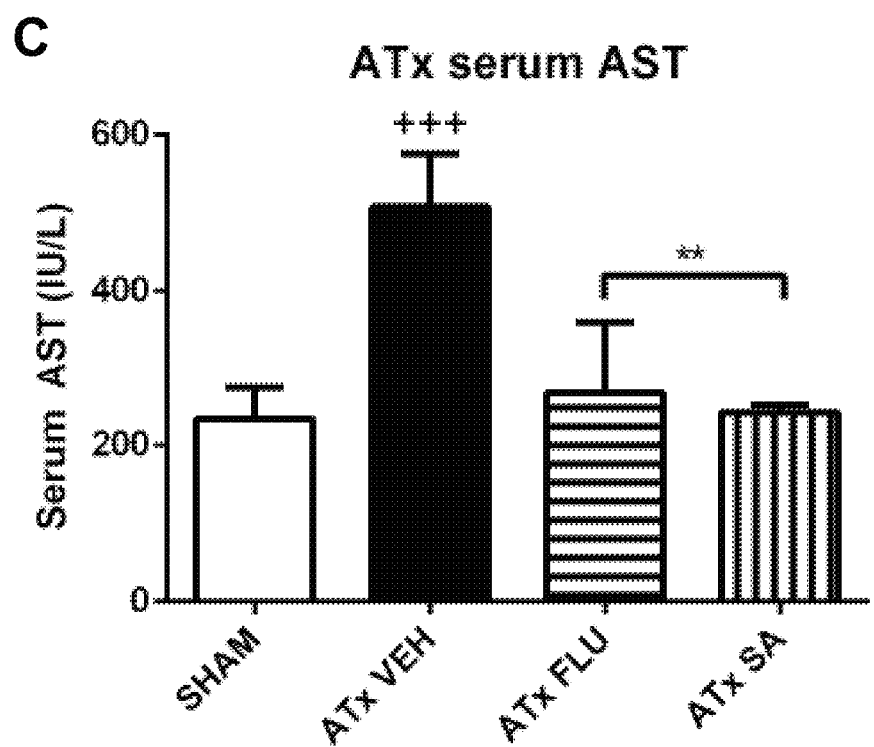
Figure 2:
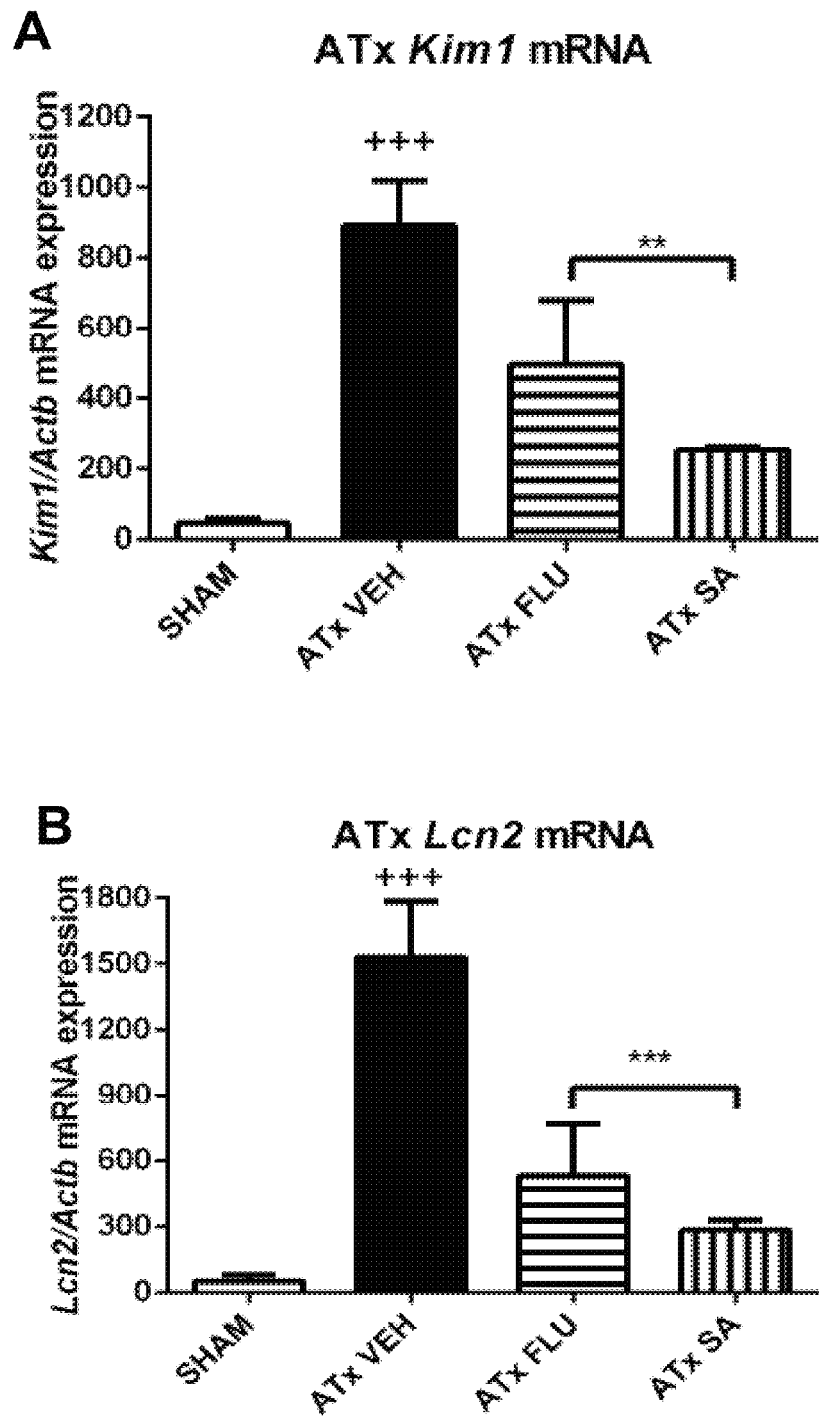
FIG. 2. S1R agonism decreases ATx-induced tubular damage.
Figure 2:
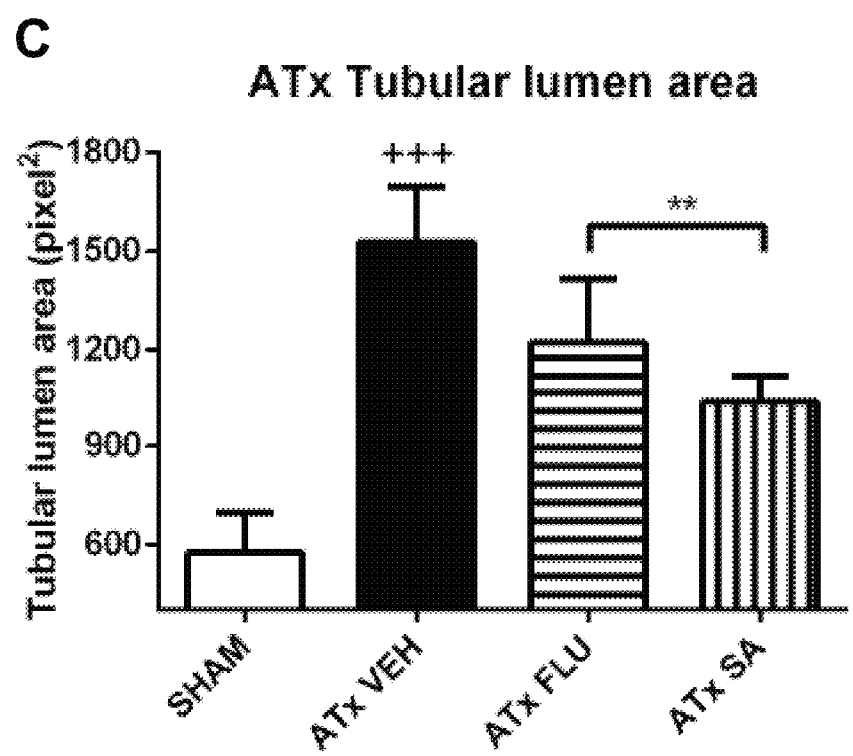
Figure 2:
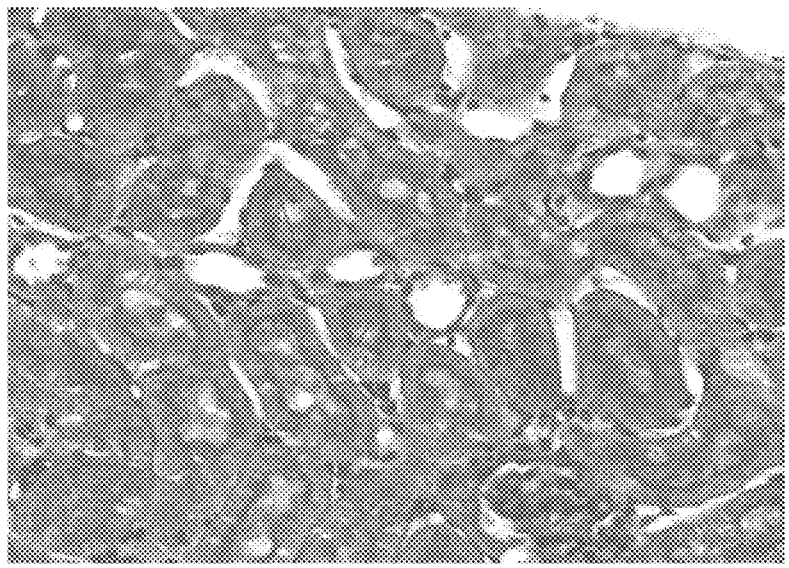
Figure 2:
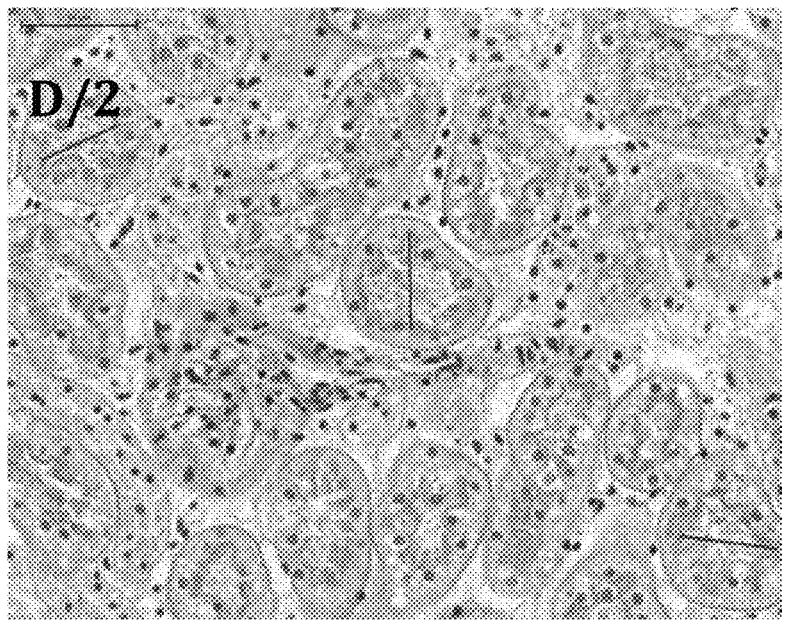
Figure 2:
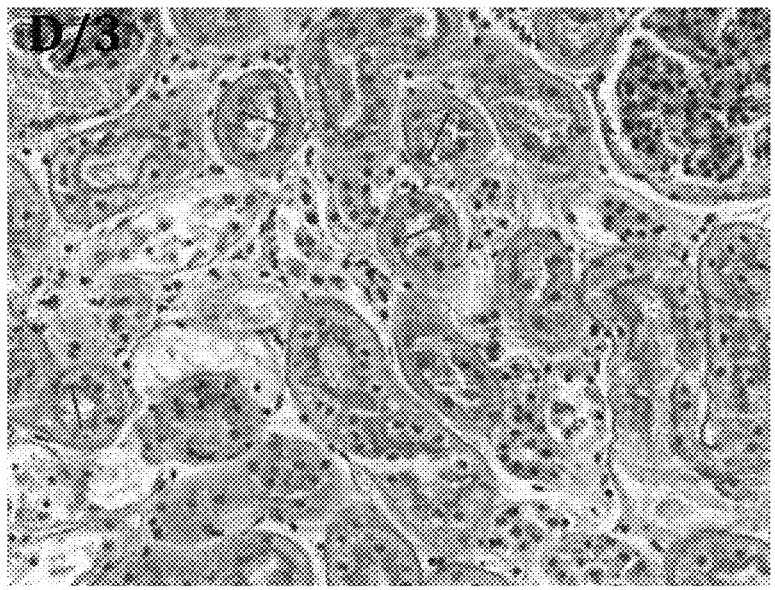
Figure 2:
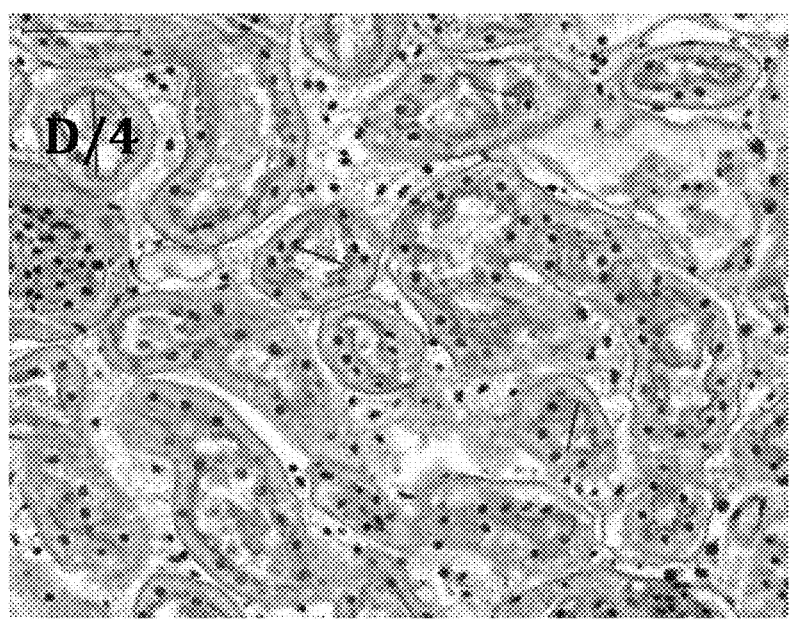

Analysis of pictures of PAS-stained kidney sections showed that tubular and glomerular injury was severe in kidneys treated with conventional preservation fluid. Glomeruli were collapsed, their structure was damaged and degraded. Excessive signs of necrosis and picnotic nuclei were observed in tubular epithelial cells. Kidneys stored in a fluvoxamine containing preservation solution showed milder histological damage. Glomeruli were intact, tubular nuclei and plasma showed normal staining. Tubular brush borders were preserved. (FIG. 2)

Addition of an S1R Agonist Compound to the Preservation Solution Inhibits Apoptosis Apoptosis Markers (i) Storage: fluvoxamine, SA 4503 and PRE-084 decreased mRNA levels of BAX, an apoptotic activator protein, in the stored kidneys, although the difference is not statistically significant. Fluvoxamine treatment markedly increased mRNA levels of Bcl-2, an anti-apoptotic protein. PRE-084 had a similar effect, while no such effect could be shown for SA 4503 (FIG. 7C).

Levels of cleaved caspase (319 kDa form) are decreased by fluvoxamine both in Custodiol and saline, and a tendency of decrease is evident in HT.

(ii) Transplantation after storage. The effect of fluvoxamin is clearly indicated by a significant decrease of BAX expression (FIG. 3B) and a significant increase of mRNA levels of Bcl-2 (FIG. 3C).

TUNEL-Staining (ii) Transplantation after storage. Apoptotic cells were detected in a TUNEL assay. Vehicle treated kidneys showed extended apoptotic areas, while the glomeruli of fluvoxamine treated kidneys showed significantly less apoptotic cells (FIG. 3A, D1-D3).

Addition of an S1R Agonist Compound to the Preservation Solution Affords Protection Against Cellular Stress Via Induction of Heat-Shock Proteins Heme oxygenase-1 (HO-1), a heat shock protein, expression is induced by oxidative stress, e.g. ischemia not only in the kidney, but in other organs, such as the heart, liver. etc.

(ii) Transplantation after storage. Vehicle treatment dramatically increased expression of HO-1, which was prevented by fluvoxamine.

Addition of an S1R Agonist Compound to the Preservation Solution Improves Kidney Function after (i) Storage and (ii) Storage and Subsequent Transplantation.

Early Markers of Kidney Injury

Proximal tubular injury marker Kidney Injury Molecule-1 (KIM-1) is a type 1 transmembrane protein, with an immunoglobulin and mucin domain, whose expression is markedly upregulated in the proximal tubule in the post-ischemic rat kidney. KIM-1 expressing PTEC (proximal tubular epithelial cells) as residential phagocytes, contribute to the removal of apoptotic cells and facilitate the regeneration of injured tubules. The proximal tubule is especially sensitive to ischemia, making KIM-1 a good early marker.

Monocyte chemoattractant protein-1 (MCP-1) is another biomarker known to be upregulated in renal injury. It is one of the key chemokines that regulate migration and infiltration of monocytes or macrophages.

Renal neutrophil gelatinase-associated lipocalin (NGAL) is a specific indicator of kidney injury that correlates with the severity of renal impairment. In case of acute kidney injury, NGAL is secreted in high levels into the blood and urine within a few hours of injury but it is detectable in chronic kidney disease as well. It is indicative of the presence and also the severeness of kidney injury. NGAL may be measured from serum or urine.

(i) Storage. KIM-1 levels are decreased dramatically in isolated kidneys stored in Custodiol and fluvoxamine compared to vehicle treatment (FIG. 6A). Addition of NE100 to the preservation fluid diminished the protective effect of fluvoxamine. Both SA 4503 and PRE-084 inhibited the increase of KIM-1, although the effect of fluvoxamine is more pronounced. The effect of fluvoxamine in saline was milder, though a tendency of decrease is noticed.

MCP-1 levels were less elevated as measured after storage in fluvoxamine containing preservation solution in comparison to conventional Custodiol. Similar results are seen with PRE-084.

NGAL mRNA expression is decreased by all three S1R agonists tested in Custodiol compared to vehicle treatment. Efficacy of fluvoxamine in saline was also demonstrated.

(ii) Transplantation after storage. KIM-1 expression levels markedly increased in vehicle treated rats after transplantation as compared to sham operated animals, indicating ischemic injury. Fluvoxamine and SA 4503 treatment resulted in a significantly lower expression as measured after transplantation.

Levels of MCP-1 were also significantly less elevated in fluvoxamine treated autotransplanted kidneys.

Fluvoxamine and SA 4503 treatment significantly decreased NGAL levels compared to Custodiol (FIG. 2B).

Functional Parameters (ii) Transplantation after storage. Kidney function was substantially improved in both fluvoxamine and SA 4503 treated rats as shown by lower serum creatinine and AST levels as compared to the preservation solution without an S1R agonist compound. Furthermore, SA 4503 significantly decreased BUN (Blood urea nitrogen) levels as well.

Anti-Inflammatory Effect

S1R agonism had anti-inflammatory effects in the stored and subsequently transplanted kidney as shown by both decreased mRNA levels and protein levels of inflammatory cytokines (IL10, IL-1α, TNFα) in fluvoxamine treated kidneys.

Addition of an S1R Agonist Compound to the Preservation Solution Protects Liver Cells Against Cold Ischemia During Storage Histological integrity of the isolated livers was preserved by the addition of an SR1 agonist compound to the preservation solution even after 8 hours of cold storage as shown by the number of cytoplasmic vacuoles. (FIG. 9)

S1R agonists for use in the present invention can be prepared according to methods known for a person skilled in the art or are commercially available like fluvoxamine, SA4503, PRE-084, 4-IBP, ANAVEX2-73, etc.

For example, fluvoxamine maleate can be prepared as described in U.S. Pat. Nos. 4,085,225 and 6,433,225 B1. Compound having a similar structure as fluvoxamine may be prepared as described in e.g. U.S. Pat. Nos. 3,692,835, 4,081,551A, 4,085,225A, 4,086,361A or 4,077,999. The skilled person is aware of the appropriate methods to synthetise the compounds according to formula I', II, III, IV or V based on the guidance of the aforementioned patents and his/her general knowledge in the field.

EP2353598A1 discloses synthesis of sigma-receptor ligands including cumetasine and related compounds.

PRE-084 is a high affinity, S1R agonist, selective for the S1R subtype (Kis=2.2 and 13,091 nM for σ1 and σ2 receptors, respectively). It is a potent ligand of the S1R (IC50=44 nM) without appreciable affinity for PCP receptors (IC50>100,000 nM) and its availability is described e.g. [Griesmaier E et al. Experimental Neurology 237(2), 388-395 (2012)]. Rossi, Daniela et al. describe the synthesis of sigma-receptor ligands based on arylalkenylaminic scaffold, among others RC-33, see Table A [Rossi D et al. Bioorganic & Medicinal Chemistry 19(21), 6210-6224 (2011)]. PRE-084 and structural analogues can be prepared as described in WO 1992002481 A1. Modifications to the synthesis of a desired compound are known to the skilled person.

It is known for a large number of compounds that they are S1R agonist. To test binding affinity and measure dissociation constant can be done by usual methods in protein and bioorganic chemistry.

For example Xu, Rong et al. disclose the effect of ether modifications to SA 4503 on binding affinity and selectivity for SR and monoamine transporters and methods to measure these parameters [Rong Xu et al. Bioorganic & Medicinal Chemistry 23(1), 222-230 (2015)].

Furthermore, Rossi, Daniela et al. (see above) selected and identified a potent and selective S1R agonist among a number of compounds and described related methods. Moreover, the authors have developed a three dimensional S1R pharmacophore model using active compounds only to derive this model. The model included two hydrophobes and a positive nitrogen as relevant features and it was able to discriminate between molecules with and without affinity toward S1R subtype. Thus, it is well within the skills of a person skilled in the art to prepare and select compounds according to the invention.

It is well within the skills of a person skilled in the art to test whether a potential S1R agonist is actually an agonist.

A usual method to test whether an S1R agonist acts on the S1R is to use a specific antagonist, as a control. Such a well-accepted specific antagonist is NE-100 which is a potent and selective S1R antagonist (Ki=0.86 nM) that displays >55-fold selectivity over S2R and >6000-fold selectivity over D1, D2, 5-HT1A, 5-HT2 and PCP receptors (4-Methoxy-3-(2-phenylethoxy)-N,N-dipropylbenz-eneethanamine hydrochloride). NE-100 exhibits reversible binding (Kd=1.2 nM) [Okuyama S et al. CNS Drug Rev. 2(2), 226-237 (1999), Berardi F et al. Bioorg. Med. Chem. 9(5), 1325-35 (2001)].

Concentration of the S1R agonist compound in the preservation solution. The concentration of fluvoxamine in the experiments described herein was selected to be well below the usual daily dose administered in the treatment of depression. Guidance for the calculation of "human" doses and concentrations may be found in international and national guidelines, e.g. in guidelines provided by the Food and Drug Administration, e.g. in Guidance for Industry Estimating the Maximum Safe Starting Dose in Initial Clinical Trials for Therapeutics in Adult Healthy Volunteers.

EXAMPLES

Examples

Methods

Compounds

Fluvoxamine (fluvoxamine maleate, Sigma Aldrich, St. Louis, MO, USA), PRE-084 (2-morpholin-4-dylethyl 1-phenylcyclohexane-1-carboxylate Sigma Aldrich, St. Louis, MO, USA), SA4503 (1-[2-(3,4-Dimethoxyphenyl) ethyl]-4-(3-phenylpropyl)piperazine; Tocris Bioscience, Bristol, UK); NE100 (N-dipropyl-2-[4-methoxy-3-(2-phenylethoxy)-phenyl]-ethylamine monohydrochloride, Tocris Bioscience, Bristol, UK)

Rat Model of Kidney Isograft Autotransplantation

Animals

The institutional committee on animal welfare approved all experiments. Experiments were performed on Male Wistar rats weighing 205±15 g (Toxi-Coop Toxicological Research Center, Dunakeszi, Hungary). Animals were housed in a temperature-controlled (22±1° C.) room with alternating light and dark cycles and had free access to standard rat chow and water.

Male Wistar rats (n=8/group) were anesthetized with isoflurane (3% vol/vol) mixed with synthetic air (1 L/min) before surgery and placed on a temperature-controlled table to maintain core body temperature. Left kidneys were perfused with cold Custodiol perfusion solution (Na$^+$: 15 mmol/L; K$^+$: 9 mmol/L; Mg$^{2+}$: 4 mmol/L; Ca$^{2+}$: 0.015 mmol/L; histidine: 198 mmol/L; tryptophan: 2 mmol/L; ketoglutarate: 1 mmol/L; mannitol: 30 mmol/L) (Franz Kohler Chemie GMBH, Bensheim, Germany), then removed from the animal: kidneys were placed into a container for 2 hours filled with either (i) cold Custodiol perfusion solution (ATx) or (ii) cold Custodiol perfusion solution containing 0.003 mg/mL FLU (ATx FLU) or (iii) cold Custodiol perfusion solution containing 0.003 mg/mL SA4503 (ATx SA). After 2 hours kidneys were placed back into the rats and end-to-end anastomoses of the renal artery, vein and ureter were performed. Contralateral kidneys were removed and the autotransplanted kidneys were observed to ensure reperfusion. Total warm ischemia time was 35 min in all animals. Sham operated animals served as controls.

After 24 hours of reperfusion, blood samples were collected from the abdominal aorta, the remnant kidneys were harvested, instantly snap-frozen in liquid nitrogen, and stored at −80° C. or fixed in buffered 8% formalin for further processing. The experimental design of the autotransplantation is shown in FIG. 9

Rat Model of Kidney and Liver Cold Ischemia

Male Wistar rats were anesthetized with isoflurane (3% vol/vol) mixed with synthetic air (1 L/min) before surgery and placed on a temperature-controlled table to maintain core body temperature. Kidneys (n=6/group) were washed through the renal arteries with 5 ml cold solution, then removed from the animal and placed into a container filled with the same solution for either 2 or 3 hours. The following perfusion solutions were used: (i) Custodiol, 2 hours of cold perfusion (Cust. 2h CP); (ii) Custodiol containing 0.003 mg/mL FLU, 2 hours of cold perfusion (Cust. 2h CP+FLU); (iii) Custodiol containing 0.003 mg/mL SA4503, 2 hours of cold perfusion (Cust. 2h CP+SA); (iv) Custodiol containing 0.003 mg/mL PRE-084, 2 hours of cold perfusion (Cust. 2h CP+PRE); (v) Custodiol containing 0.003 mg/mL FLU and 0.001 mg/mL NE100, 2 hours of cold perfusion (Cust. 2h CP+FLU+NE100); (vi) Custodiol containing 0.001 mg/mL NE100, 2 hours of cold perfusion (Cust. 2h CP+NE100); (vii) Custodiol, 3 hours of cold perfusion (Cust. 3h CP); (viii) Custodiol containing 0.003 mg/mL FLU, 3 hours of cold perfusion (Cust. 3h CP+FLU); (ix) Saline, 2 hours of clod perfusion (Saline 2h CP); (x) Saline containing 0.003 mg/mL FLU, 2 hours of cold perfusion (Saline+FLU 2h CP); (xi) HypoThermosol® FRS preservation solution (Trolox, $Na^+$, $K^+$, $Ca^{2+}$, $Mg^{2+}$, $Cl^-$, $H_2PO_4^-$, HEPES, lactobionate, sucrose, mannitol, glucose, dextran-40, adenosine, glutathione; PCT patent application number: PCT/GB2009/051659) (Sigma Aldrich, St. Louis, MO, USA), 2 hours of cold perfusion (HT 2h CP); (xii) HypoThermosol® FRS containing 0.003 mg/mL FLU, 2 hours of cold perfusion (HT 2h CP+FLU). After cold ischemia kidneys were immediately snap-frozen in liquid nitrogen and stored at −80° C. or fixed in buffered 8% formalin for further processing.

For liver storage experiments livers were removed from the animal and placed into a container filled with the same solution for 8 hours (i.e. Custodiol containing 0.003 mg/mL FLU, Custodiol containing 0.003 mg/mL SA4503 and Custodiol containing 0.003 mg/mL PRE-084).

Measurement of Metabolic and Renal Parameters

Metabolic (glucose, fructosamine, total and HDL-cholesterol, triglycerides) and renal functional parameters from rat sera (sodium, potassium, creatinine, blood urea nitrogen (BUN), aspartate transaminase (AST)) were determined with commercially available kits on a Hitachi 912 photometric chemistry analyzer.

Histological Analysis

Kidneys were fixed in 8% formalin, embedded into paraffin and 5 μm sections were stained with periodic acid-Schiff (PAS) to assess tubular injury. Images were taken with Panoramic Viewer (3DHISTECH Ltd., Budapest, Hungary). Tubular luminal areas were measured in three fields of magnification ×200 per rat. The analysis was performed in a double-blinded fashion with computer-assisted morphometry using Adobe Photoshop CS6 (Adobe Systems Corporation, San José, Calif., USA) and Image J (*National Institute of Health,* Bethesda, MD, USA) softwares on a Zeiss Axiolmager A1 light-microscope (Carl Zeiss A G, Jena, Germany).

Liver samples were immersed in 10% buffered formalin. After 24 hours, the samples were embedded in paraffin, cut into 5-μm sections and stained with hematoxylin and eosin.

Apoptosis Detection by TUNEL Assay

Formalin-fixed kidney samples were embedded into paraffin. 5 μm thick sections were mounted on Superfrost slides (Thermo Shandon, Runcorn, UK) and were manually deparaffinized. Assay was performed using the Apoptag® Peroxidase In situ Apoptosis Detection Kit (Millipore, Billerica, MA, USA). Briefly, samples were pretreated with Proteinase K for 15 min. Following repeated washing steps endogenous peroxidase activity was blocked by 3% H2O2 in methanol for 5 min at room temperature. Next, slides were incubated in reaction buffer containing 30% TdT enzyme for 1 hour at room temperature after which Stop buffer was added. Slides were incubated with anti-Dioxigenin Conjugate for 30 min at room temperature. Slides were developed using DAB peroxidase substrate. The areas of TUNEL-positive apoptotic nuclei were measured in three fields of magnification ×200 per rat. The analysis was performed using Adobe Photoshop CS6 (Adobe Systems Corporation, San José, Calif., USA) and Image J (National Institute of Health, Bethesda, MD, USA) softwares on a Zeiss Axiolmager A1 light-microscope (Carl Zeiss A G, Jena, Germany).

Immunohistochemistry

Formalin-fixed kidney samples were embedded into paraffin. One to two micron thick sections were mounted on Superfrost slides (Thermo Shandon, Runcorn, UK) and were manually deparaffinized. Endogenous peroxidase activity was blocked by 3% $H_2O_2$ in methanol for 20 min at room temperature. Slides were immersed in 0.05 mM citrate buffer (pH=6) and exposed to 93° C. for 10 min (MFX-800-3 automatic microwave, Meditest, Budapest, Hungary). Slides were primarily treated with anti-CD45 antibody (Abcam, Cambridge, UK) diluted to 1:100 and incubated overnight at 4° C. After washing, secondary antibody Biotinylated Link (Dako, Glostrup, Denmark) was used and incubated for 15 min at room temperature. For visualization a standard avidin-biotin peroxidase technique (ABC system, Dako, Glostrup, Denmark) was used with aminoethyl carbazole as chromogen.

Quantitative Real Time-PCR

Total RNA was isolated from kidneys with GeneAid Total RNA Mini Kit (Geneaid Biotech Ltd., New Taipei City, Taiwan). 500 ng RNA was reverse-transcribed using Maxima First Strand cDNA Synthesis Kit for RT-qPCR (Thermo Scientific, Waltham, MA, USA) to generate first-strand cDNA. mRNA expressions of Ngal (Lcn2), Kim1, Mcp1, IL-1α (Il1α), IL-6 (Il6), IL-10 (Il10), TNF-α (Tnf), HO-1 (Hmox1), Bax, Bcl-2 (Bcl2), 18S ribosomal RNA (Rn18s) and β-actin (Actb) were determined with real-time RT-PCR using Light Cycler 480 SYBR Green 1 Master enzyme mix on a Light Cycler system (Roche Diagnostics, Mannheim, Germany). The reaction mix contained 10 pmol/μl of each PCR primer (Table 1; Integrated DNA Technologies Inc., Coralville, IA, USA), 10 μl of Light Cycler 480 SYBR Green 1 Master enzyme mix and 1 μl of cDNA sample. The conditions of the PCRs were as follows: 1 cycle at 95° C. for 5 minutes, followed by 70 cycles under the appropriate PCR conditions. Quantification was performed with the second-derivative method by monitoring the cycle number at which the fluorescent sign could be distinguished from the background. Results were analyzed with Light Cycler 480 software version 1.5.0.39 (Roche Diagnostics, Mannheim, Germany). The mRNA expression of each gene was determined by comparison to 18S ribosomal RNA as housekeeping gene from the same sample.

TABLE 1

Nucleotide sequence of specific primer pairs applied for the real time detection of examined genes and conditions of the PCR reactions.

| Gene | Primer sequences | PCR conditions |
|---|---|---|
| Rat Lcn2 | F: 5'-GGG CTG TCC GAT GAA CTG AA-3' (SEQ ID NO: 1)<br>R: 5'-CAT TGG TCG GTG GGA ACA GA-3' (SEQ ID NO: 2) | 95° C. - 5 sec<br>56° C. - 5 sec<br>72° C. - 5 sec |
| Rat Kim1 | F: 5'-CGC AGA GAA ACC CGA CTA AG-3' (SEQ ID NO: 3)<br>R: 5'-CAA AGC TCA GAG ACC CCA TC-3' (SEQ ID NO: 4) | 95° C. - 5 sec<br>60° C. - 7 sec<br>72° C. - 7 sec |
| Rat Mcp1 | F: 5'-ATG CAG TTA ATG CCC CAC TC - 3' (SEQ ID NO: 5)<br>R: 5'-TTC CTT ATT GGG GTC ACC AC - 3' (SEQ ID NO: 6) | 95° C. - 5 sec<br>60° C. - 5 sec<br>72° C. - 10 sec |
| Rat Il1α | F: 5'-TCT GCC ATT GAC CAT CTG TCT CTG -3' (SEQ ID NO: 7)<br>R: 5'-ACC ACC CGG CTC TCC TTG AA - 3' (SEQ ID NO: 8) | 95° C. - 5 sec<br>55° C. - 5 sec<br>72° C. - 5 sec |
| Rat Il6 | F: 5'-GCC ACT GCC TTC CCT ACT TC - 3' (SEQ ID NO: 9)<br>R: 5'-GCC ATT GCA CAA CTC TTT TCT C -3' (SEQ ID NO: 10) | 95° C. - 5 sec<br>55° C. - 5 sec<br>72° C. - 5 sec |
| Rat Il10 | F: 5'- AGA ACC ATG GCC CAG AAA TCA AG-3' (SEQ ID NO: 11)<br>R: 5'-ACA GGG GAG AAA TCG ATG ACA GC-3' (SEQ ID NO: 12) | 95° C. - 5 sec<br>55° C. - 5 sec<br>72° C. - 5 sec |
| Rat TNFα | F:5'-GGG GCC ACC ACG CTC TTC TGT - 3' (SEQ ID NO: 13)<br>R: 5'-CTC CGC TTG GTG GTT TGC TAC GAC -3' (SEQ ID NO: 14) | 95° C. - 5 sec<br>60° C. - 5 sec<br>72° C. - 7 sec |
| Rat Hmox1 | F: 5'- AGA CCG CCT TCC TGC TCA ACA TT -3' (SEQ ID NO: 15)<br>R: 5'- GAT TTT CCT CGG GGC GTC TCT G -3' (SEQ ID NO: 16) | 95° C. - 5 sec<br>58° C. - 5 sec<br>72° C. - 10 sec |
| Rat Bax | F: 5'- AGC CGC CCC AGG ACG CAT CCA -3' (SEQ ID NO: 17)<br>R: 5'- CAG CCG CTC CCG GAG GAA GTC AG-3' (SEQ ID NO: 18) | 95° C. - 5 sec<br>63° C. - 5 sec<br>72° C. - 10 sec |
| Rat Bcl | F: 5'- ATG GCG CAA GCC GGG AGA ACA G -3' (SEQ ID NO: 19)<br>R: 5'- TGG CGA CAA GGG CCC GTA GAG G -3' (SEQ ID NO: 20) | 95° C. - 5 sec<br>63° C. - 5 sec<br>72° C. - 10 sec |
| Rat Rn18S | F: 5'-GCG GTC GCC GTC CCC CAA CTT CTT-3' (SEQ ID NO: 21)<br>R: 5'- GCG CGT GCA GCC CCG GAC ATC TA -3' (SEQ ID NO: 22) | 95° C. - 5 sec<br>60° C. - 5 sec<br>72° C. - 10 sec |
| Rat Actb | F: 5'-ACCGAGCATGGCTACAGCGTCACC-3' (SEQ ID NO: 23)<br>R: 5'-GTGGCCATCTCTTGCTCGGAGTCT-3' (SEQ ID NO: 24) | 95° C. - 5 sec<br>54° C. - 5 sec<br>72° C. - 5 sec |

Protein Isolation and Western Blotting

All reagents for Western blotting were purchased from Bio-Rad Laboratories, Hercules, CA, USA unless stated otherwise. Tissue samples were lysed in buffer containing leupeptin, aprotinin, Triton X-100, Tris-HCl, Ethylene glycol-bis (2-aminoethylether),N,N,N',N'-tetraacetic-acid, NaF, Phenylmethylsulphonylfluoride and Na-orthovanadate (each substance were purchased from Sigma-Aldrich Co., St. Louis, MO, USA). Protein concentrations were determined using Bradford assay. Fifty micrograms of protein was separated on 12.5% SDS-PAGE gels at 200 V (~60 mA, 90 min). Pre-stained protein mixture was used as marker of molecular mass. The separated proteins were transferred into nitrocellulose membranes. Non-specific binding sites were blocked in 5% non-fat dry milk containing blot solution. Membranes were incubated with monoclonal antibody specific to rat cleaved caspase-3 (Asp175) (Cell Signaling Technology, Danvers, MA, USA) diluted to 1:1000. Blots were washed and incubated (1 hour, room temperature) with peroxidase-conjugated goat anti-rabbit IgG secondary antibody (Cell Signaling Technology, Danvers, MA, USA) diluted to 1:4000. Equal protein loading to the gel was confirmed by Ponceau S staining and an internal control was used as well Immunoreactive bands were visualized using enhanced chemiluminescence Western blotting detection protocol (Luminata™ Forte Western HRP Substrate, Millipore, Billerica, MA, USA). Bands were analyzed with Quantity One software version 4.6.9. Protein abundance was represented as Integrated Optical Density (IOD)/Ponceau S compared to controls.

Cytometric Bead Array

All reagents and equipment for CBA were purchased from BD Biosciences (Budapest, Hungary). Perfused kidney homogenates were measured for TNFα, IL-1α, and IL-10 peptide levels using appropriate rat CBA Flex Sets according to the manufacturer's protocol. Measurements were performed using a FACS Verse flow cytometer and data were analyzed using FCAP Array software.

Statistical Analysis

Data were analyzed using GraphPad Prism software (GraphPad Software Inc., La Jolla, CA, USA). After testing the normality with Kolmogorov-Smirnov test, numerical datasets from all experiments were analyzed using the Mann-Whitney U-test for two group's comparison and Kruskal-Wallis test when there were 3 or more groups. P values less than 0.05 were considered to indicate statistically significant differences. Values for all measurements were expressed as mean+−SEM.

Results of the Histologic Evaluation After Autotransplantation

Histologic evaluation after KTx was performed on PAS-stained kidney sections. Severe tubular and glomerular injury was observed in vehicle-treated rats (CP+T24 Tx). Glomeruli were collapsed, their structure was damaged and degraded. Excessive signs of necrosis and picnotic nuclei were observed in tubular epithelial cells. FLU-treated kidneys (CP+T24 Tx F) showed milder histological damage. Glomeruli were intact, tubular nuclei and plasma showed normal staining. Tubular brush borders were preserved. Similarly, structure was better preserved in kidneys that were perfused with FLU (CP F), but harvested after 2 hours of cold ischemia (CP). The degree of tubular damage was quantified by measuring tubular lumen areas. Dilatation of the tubular lumen is caused by degradation of tubular epithelial cells and is a good indicator of tubular damage. Tubular lumens were less dilated in FLU-treated kidneys with (CP+T24 Tx F) or without (CP F) reperfusion.

REFERENCES

Guibert et al Organ Preservation: Current Concepts and New Strategies for the Next Decade Transfus Med Hemother 2011; 38:125-142.

Stewart Z A, Cameron A M, Singer A L, Montgomery R A, Segev D L: Histidine-Tryptophan-Ketoglutarate (HTK) is associated with reduced graft survival in deceased donor livers, especially those donated after cardiac death. Am J Transplant 2009; 9:286-293.

Erkasap S, Ates E. L-Arginine-enriched preservation solution decreases ischaemia/reperfusion injury in canine kidneys after long term cold storage. Nephrology Dialysis Transplant 2000; 15: 1224-7

Castaneda M P, Swiatecka-Urban A, Mitsnefes M M et al. Activation of mitochondrial apoptotic pathways in human renal allografts after ischemia reperfusion injury. Transplantation 2003; 76: 50-54

Jani A, Zimmerman M, Martin J, Lu L, Turkmen K, Ravichandran K, Pacic A, Ljubanović D, Edelstein C L. Perfusion storage reduces apoptosis in a porcine kidney model of donation after cardiac death. Transplantation. 2011; 91:169-175

Stubenitsky et al. Kidney preservation in the next millenium Transpl Int (1999) 12:83-91

Moers et al. Non-heart beating organ donation: overview and future perspectives Transplant International doi: 10.1111/j.1432-2277.2007.00455.x US Renal Data System Annual Report 2015

Hosszu et al. Sigma-1 receptor agonism is protective against renal ischemia/reperfusion injury JASN ASN.2015070772; published ahead of print Apr. 7, 2016

Vettel et al. Dopamine and Lipophilic Derivates Protect Cardiomyocytes against Cold Preservation Injury. J Pharmacol Exp Ther 348:77-85, January 2014

Wu et al. Antiapoptotic compound to enhance hypothermic liver preservation. Transplantation. 1997 Mar. 27; 63(6): 803-9.

Campbell et al. Development of pancreas storage solutions: Initial screening of cytoprotective supplements for β-cell survival and metabolic status after hypothermic storage. Biopresery Biobank. 2013 February; 11(1):12-8. doi: 10.1089/bio.2012.0023.

Jani et al. Perfusion storage reduces apoptosis in a porcine kidney model of donation after cardiac death. Transplantation. 2011 Jan. 27; 91(2):169-75.

2007 Annual Report of the U.S. Organ Procurement and Transplantation Network and the Scientific Registry of Transplant Recipients: Transplant Data 1997-2006. Health Resources and Services Administration, Healthcare Systems Bureau, Division of Transplantation, Rockville, MD.

Becker T, Ringe B, Nyibata M, et al. Pancreas transplantation with histidine-tryptophan-ketoglutarate (HTK) solution and University of Wisconsin (UW) solution: is there a difference? *Jop.* 2007; 8(3):304-311.

Potdar S, Malek S, Eghtesad B, et al. Initial experience using histidine-tryptophan-ketoglutarate solution in clinical pancreas transplantation. *Clin Transplant.* December 2004; 18(6):661-665.

Mangus R S, Tector A J, Agarwal A, Vianna R, Murdock P, Fridell J A. Comparison of histidine-tryptophan-ketoglutarate solution (HTK) and University of Wisconsin solution (UW) in adult liver transplantation. *Liver Transpl.* February 2006; 12(2):226-230.

Feng L, Zhao N, Yao X, et al. Histidine-tryptophan-ketoglutarate solution vs. University of Wisconsin solution for liver transplantation: a systematic review. *Liver Transpl.* August 2007; 13(8):1125-1136.

Kloutz et al. Protection of cellular and mitochondrial functions against liver ischemia by N-benzyl-N'-(2-hydroxy-3,4-dimethoxybenzyl)-piperazine (BHDP), a signal ligand. Eur J Pharmacol 578 (2008) 292-299.

The invention claimed is:

1. A method for reducing or delaying cellular damage that occurs during ex vivo storage of a transplantable whole or partial organ or tissue, the method comprising (i) contacting the whole or partial organ or tissue ex vivo with a composition comprising an amount of a sigma 1 receptor (S1R) agonist compound effective in reducing or delaying cellular damage of said transplantable whole or partial organ or tissue during ex vivo storage and a physiologically acceptable solution suitable for ex vivo organ preservation, (ii) maintaining the transplantable whole or partial organ or tissue ex vivo in said composition before transplantation, wherein the transplantable whole or partial organ or tissue is maintained at a temperature of from 0° C. to 10° C., and wherein the S1R agonist compound has the following formula I':

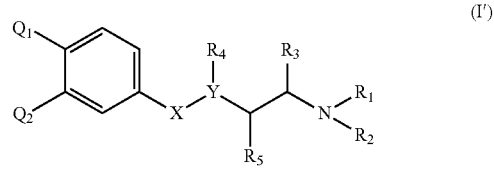

(I')

wherein $Q_1$ is H, halogen, pseudo-halogen, C(1-4) alkyl optionally substituted with 1, 2, 3 or 4 halogen(s), C(1-3) alkoxy, C(6-10) aryl, optionally substituted with 1, 2, 3 or 4 halogen(s), $Q_2$ is H, halogen, pseudo-halogen or C(1-3) alkoxy, X is O, $CH_2$, ethylene or carbonyl (CO), amide or not present, or X has the formula

wherein $R_6$ is selected from the group consisting of a hydroxyl, substituted or unsubstituted C(1-6) alkyl, C(1-6) alkoxy, or C(1-6) alkoxyalkyl, and C(5-10) aryl, or X has the formula

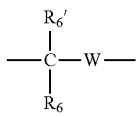

wherein W is —CH— or carbonyl (—CO—) or W is not present, and
$R_6$ and $R_6'$ are independently substituted or unsubstituted C(1-6) alkyl, C(1-6) alkyloxy, C(1-6) alkoxyalkyl, C(1-6) alkyloxy carbonyl, or at least one of $R_6$ and $R_6'$ is a C(5-10) aryl,
or $R_6$ and $R_6'$ together form a C(4-7) cycloalkyl,
or X has the formula

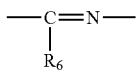

wherein $R_6$ is selected from a substituted or unsubstituted C(1-6) alkyl, C(1-6) alkoxy, or C(5-10) aryl,
Y is CH, N or O, —O—$CH_2$—$CH_2$—O— or not present
wherein
if Y is O then $R_4$ is not present,
if Y is N then $R_4$ is H, or a C(1-3) alkyl or C(1-3) alkenyl, or $R_4$ and $R_1$ together with Y, N and the carbon atoms between them form a C(5-7) heterocyclic ring,
if Y is CH then $R_4$ is selected from a H, substituted or unsubstituted C(1-4) alkyl, C(1-4) alkoxy and C(5-10) aryl, or $R_4$ and $R_1$ together with Y, N and the carbon atoms between them form a C(5-7) heterocyclic ring,
$R_3$ is selected from H, a substituted or unsubstituted C(1-6) alkyl, C(1-6) alkoxy, C(5-10) aryl, or
$R_3$ and the —X—Y—C2- alkyl moiety, via $R_6$, may form a saturated or partially unsaturated 6 to 8 membered cycloalkyl or 6 to 8 membered heterocycloalkyl comprising 0 to 3 heteroatom(s), or
$R_3$ and the —X—Y—C2- alkyl moiety, via $R_6$, may form a substituted or unsubstituted C(7-14) polycyclic aryl or C(7-14) polycyclic heteroaryl or C(7-14) cycloalkylaryl, or
$R_3$ and the —Y—C2- alkyl moiety, via $R_4$, may form a saturated or partially unsaturated 6 to 8 membered cycloalkyl or 6 to 8 membered heterocycloalkyl comprising 0 to 3 heteroatom, or an alkylaryl,
$R_5$ is H, C(1-3) alkyl or C(1-3) alkyloxy or
$R_5$ and $R_6$ together with carbon atoms which they are attached to form a 3, 4, 5 or 6 membered saturated or unsaturated ring, said ring optionally comprising a heteroatom,
$R_1$ and $R_2$ are independently H or a C(1-6) alkyl, or
$R_1$ and $R_2$ form a 5 or 6 membered, saturated or unsaturated ring,
said ring optionally comprising a heteroatom, or
said ring being optionally a substituted or unsubstituted piperidine ring, or
$R_1$ is a C(2-4) alkylene and together with Y and N and the carbon atoms between Y and N form a heterocyclic ring, and
$R_2$ is a C(1-6) alkyl, C(5-10) aryl or C(7-10) aralkyl,
or $R_2$ is a C(2-4) alkylene and together with the N form a heterocyclic ring,
or a pharmaceutically acceptable salt thereof.

2. The method according to claim 1, wherein the organ is selected from heart, lung, abdominal organs, or cornea.

3. The method according to claim 1, wherein the organ is the kidney or the tissue is renal tissue.

4. The method according to claim 1, wherein the organ is the liver or the tissue is hepatic tissue.

5. The method according to claim 1, wherein
$Q_1$ is H, halogen, pseudo-halogen, C(1-4) alkyl optionally substituted with 1, 2, 3 or 4 halogen(s), C(1-3) alkoxy, C(6-10) aryl, optionally substituted with 1, 2, 3 or 4 halogen(s),
$Q_2$ is H, halogen, pseudo-halogen or C(1-3) alkoxy,
X is O, $CH_2$, ethylene or carbonyl (CO), amide or not present,
or X has the formula

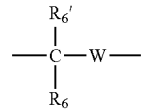

wherein
W is —CH— or carbonyl (—CO—), and
$R_6$ and $R_6'$ are independently substituted or unsubstituted C(1-6) alkyl, C(1-6) alkyloxy, C(1-6) alkoxy C(1-6) alkyl, C(1-6) alkyloxy carbonyl or at least one of $R_6$ and $R_6'$ is a C(5-10) aryl,
or $R_6$ and $R_6'$ together form a C(4-7) cycloalkyl,
or X has the formula

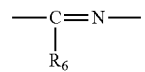

wherein
$R_6$ is selected from a substituted or unsubstituted C(1-6) alkyl, C(1-6) alkoxy, C(1-6) alkoxy C(1-6) alkyl or C(1-2) alkoxy C(1-6) alkyl or C(1-6) alkoxyalkyl, C(1-6) alkyloxy carbonyl or C(5-10) aryl,
Y is CH, N or O, —O—$CH_2$—$CH_2$—O— or not present
wherein
if Y is O then $R_4$ is not present,
if Y is N then $R_4$ is H, or a C(1-3) alkyl or C(1-3) alkenyl,
if Y is CH then $R_4$ is selected from a H, substituted or unsubstituted C(1-4) alkyl, C(1-4) alkoxy and C(5-10) aryl,
$R_3$ is selected from H, a substituted or unsubstituted C(1-6) alkyl, C(1-6) alkoxy, C(1-2) alkoxy C(1-6) alkyl or C(1-6) alkoxyalkyl, C(5-10) aryl
$R_5$ is H, C(1-3) alkyl or C(1-3) alkyloxy
$R_1$ and $R_2$ are independently H or a C(1-6) alkyl, or
$R_1$ and $R_2$ form a 5 or 6 membered, saturated or unsaturated, said ring optionally comprising a heteroatom, or said ring being optionally a substituted or unsubstituted piperidine ring.

6. The method according to claim 5, wherein
$Q_1$ is H, halogen, pseudo-halogen, C(1-2) alkyl optionally substituted with 1, 2, 3 or 4 halogen(s), C(1-2) alkoxy, C(5-6) aryl, optionally substituted with 1, 2, 3 or 4 halogen(s),
$Q_2$ is H, halogen or pseudo-halogen,
X is O, or
X has the formula

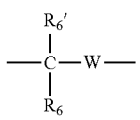

wherein
W is —CH— or carbonyl (—CO—), and
$R_6$ and $R_6'$ are independently substituted or unsubstituted C(1-3) alkyl, C(1-3) alkoxy, C(1-2) alkoxy C(1-6) alkyl, C(1-4) alkyloxycarbonyl or at least one of $R_6$ and $R_6'$,
or $R_6$ and $R_6'$ together form a C(4-6) cycloalkyl,
or X has the formula

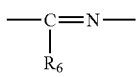

wherein
$R_6$ is selected from C(1-3) alkyl, C(1-3) alkoxy, C(1-4) alkoxy C(1-6) alkyl or C(1-6) alkoxyalkyl, C(1-4) alkyloxycarbonyl or C(5-6) aryl,
Y is O or —O—CH$_2$—CH$_2$—O—
wherein
$R_4$ is not present,
$R_3$ is selected from H, C(1-4) alkyl, C(1-4) alkoxy, C(1-2) alkoxy C(1-6) alkyl, C(1-6) alkoxyalkyl, or C(5-6) aryl
$R_5$ is H, C(1-3) alkyl or C(1-3) alkyloxy
$R_1$ and $R_2$ are independently H or a methyl or ethyl, or
$R_1$ and $R_2$ form a 5 or 6 membered, saturated or unsaturated ring, said ring optionally comprising a heteroatom, or
said ring being optionally a substituted or unsubstituted piperidine ring.

7. The method according to claim 1, wherein said S1R agonist compound has the following formula II:

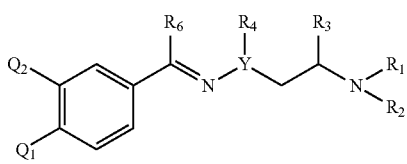

wherein
$Q_1$ is a Cl or F or a methyl substituted with halogen selected from CH$_2$F, CHF$_2$CF$_3$, CH$_2$Cl, CHCl$_2$, CCl$_3$, or methoxy
$Q_2$ is H, Cl or F,
$R_6$ is selected from a substituted or unsubstituted C(1-3) alkyl, C(1-3) alkoxy, C(1-2) alkoxy C(1-6) alkyl, C(5-6) aryl, Y is O
$R_4$ is not present,
$R_3$ is H, methyl or ethyl,
$R_5$ is H, methyl or ethyl,
$R_1$ and $R_2$ are independently H, methyl or ethyl,
or a pharmaceutically acceptable salt thereof.

8. The method according to claim 7, wherein
$Q_1$ is a methyl substituted with halogen selected from CHF$_2$, CF$_3$, CHCl$_2$ and CCl$_3$,
$Q_2$ is H,
$R_6$ is selected from a substituted or unsubstituted C(1-2) alkoxy C(2-5) alkyl,
Y is O,
$R_4$ is not present,
$R_3$ is H or methyl,
$R_5$ is H, methyl or ethyl,
$R_1$ and $R_2$ are independently H, methyl or ethyl,
or a pharmaceutically acceptable salt thereof.

9. The method according to claim 1, wherein the S1R agonist compound is selective for S1 receptors over S2 receptors.

10. The method according to claim 1, wherein the S1R agonist compound is fluvoxamine.

11. The method according to claim 3, wherein the S1R agonist compound is fluvoxamine.

12. A method for reducing or delaying cellular damage that occurs during ex vivo storage of a transplantable whole or partial organ or tissue, the method comprising
(i) contacting the transplantable whole or partial organ or tissue ex vivo with a composition comprising an amount of a sigma 1 receptor (S1R) agonist compound effective in reducing or delaying cellular damage of said transplantable whole or partial organ or tissue during ex vivo storage and a physiologically acceptable solution suitable for ex vivo organ preservation,
(ii) maintaining the transplantable whole or partial organ or tissue ex vivo in said composition before transplantation,
wherein the S1R agonist compound has the following formula I':

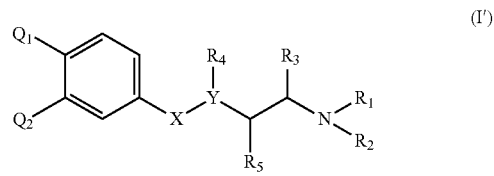

wherein
$Q_1$ is H, halogen, pseudo-halogen, C(1-4) alkyl optionally substituted with 1, 2, 3 or 4 halogen(s), C(1-3) alkoxy, C(6-10) aryl, optionally substituted with 1, 2, 3 or 4 halogen(s),
$Q_2$ is H, halogen, pseudo-halogen or C(1-3) alkoxy,
X is O, CH$_2$, ethylene or carbonyl (CO), amide or not present,
or X has the formula

wherein $R_6$ is selected from the group consisting of a hydroxyl, substituted or unsubstituted C(1-6) alkyl, C(1-6) alkoxy, or C(1-6) alkoxyalkyl, and C(5-10) aryl,
or X has the formula

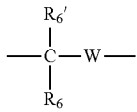

wherein W is —CH— or carbonyl (—CO—) or W is not present, and
$R_6$ and Re are independently substituted or unsubstituted C(1-6) alkyl, C(1-6) alkyloxy, C(1-6) alkoxyalkyl, C(1-6) alkyloxy carbonyl, or at least one of $R_6$ and $R_6'$ is a C(5-10) aryl,
or $R_6$ and $R_6'$ together form a C(4-7) cycloalkyl,
or X has the formula

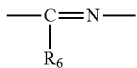

wherein $R_6$ is selected from a substituted or unsubstituted C(1-6) alkyl, C(1-6) alkoxy, or C(5-10) aryl,
Y is CH, N or O, —O—$CH_2$—$CH_2$—O— or not present wherein
if Y is O then $R_4$ is not present,
if Y is N then $R_4$ is H, or a C(1-3) alkyl or C(1-3) alkenyl, or $R_4$ and $R_1$ together with Y, N and the carbon atoms between them form a C(5-7) heterocyclic ring,
if Y is CH then $R_4$ is selected from a H, substituted or unsubstituted C(1-4) alkyl, C(1-4) alkoxy and C(5-10) aryl, or $R_4$ and $R_1$ together with Y, N and the carbon atoms between them form a C(5-7) heterocyclic ring,
$R_3$ is selected from H, a substituted or unsubstituted C(1-6) alkyl, C(1-6) alkoxy, C(5-10) aryl, or
$R_3$ and the —X—Y—C2- alkyl moiety, via $R_6$, may form a saturated or partially unsaturated 6 to 8 membered cycloalkyl or 6 to 8 membered heterocycloalkyl comprising 0 to 3 heteroatom(s), or
$R_3$ and the —X—Y—C2- alkyl moiety, via $R_6$, may form a substituted or unsubstituted C(7-14) polycyclic aryl or C(7-14) polycyclic heteroaryl or C(7-14) cycloalkylaryl, or
$R_3$ and the —Y—C2- alkyl moiety, via $R_4$, may form a saturated or partially unsaturated 6 to 8 membered cycloalkyl or 6 to 8 membered heterocycloalkyl comprising 0 to 3 heteroatom, or an alkylaryl,
$R_5$ is H, C(1-3) alkyl or C(1-3) alkyloxy or
$R_5$ and $R_6$ together with carbon atoms which they are attached to form a 3, 4, 5 or 6 membered saturated or unsaturated ring, said ring optionally comprising a heteroatom,
$R_1$ and $R_2$ are independently H or a C(1-6) alkyl, or
$R_1$ and $R_2$ form a 5 or 6 membered, saturated or unsaturated ring,
said ring optionally comprising a heteroatom, or
said ring being optionally a substituted or unsubstituted piperidine ring, or
$R_1$ is a C(2-4) alkylene and together with Y and N and the carbon atoms between Y and N form a heterocyclic ring, and $R_2$ is a C(1-6) alkyl, C(5-10) aryl or C(7-10) aralkyl,
or $R_2$ is a C(2-4) alkylene and together with the N form a heterocyclic ring,
or a pharmaceutically acceptable salt thereof,
wherein the organ is the kidney and the tissue is renal tissue,
wherein cellular damage of the kidney or the renal tissue is reduced or delayed, as indicated by a decrease of the tubular lumen area dilatation or any one of a decreased level of serum creatinine, decreased level of blood urea nitrogen, decreased level of blood KIM1, decreased level of blood MCP-1, decreased level of blood NGAL and increased glomerular filtration rate, as compared to the corresponding marker in an organ stored under identical conditions and in a preservation solution having the same composition but not comprising the S1R agonist compound.

13. The method according to claim 1, wherein the transplantable whole or partial organ or tissue is stored for at least 6 hours after the contacting and before the transplantation.

14. The method according to claim 12, wherein the kidney or renal tissue is maintained at a temperature of from 0° C. to 10° C.

15. The method according to claim 12, wherein
$Q_1$ is H, halogen, pseudo-halogen, C(1-4) alkyl optionally substituted with 1, 2, 3 or 4 halogen(s), C(1-3) alkoxy, C(6-10) aryl, optionally substituted with 1, 2, 3 or 4 halogen(s),
$Q_2$ is H, halogen, pseudo-halogen or C(1-3) alkoxy,
X is O, $CH_2$, ethylene or carbonyl (CO), amide or not present,
or X has the formula

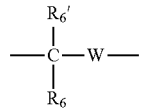

wherein
W is —CH— or carbonyl (—CO—), and
$R_6$ and $R_6'$ are independently substituted or unsubstituted C(1-6) alkyl, C(1-6) alkyloxy, C(1-6) alkoxy C(1-6) alkyl, C(1-6) alkyloxy carbonyl or at least one of $R_6$ and $R_6'$ is a C(5-10) aryl,
or $R_6$ and $R_6'$ together form a C(4-7) cycloalkyl,
or X has the formula

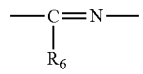

wherein
$R_6$ is selected from a substituted or unsubstituted C(1-6) alkyl, C(1-6) alkoxy, C(1-6) alkoxy C(1-6) alkyl or C(1-2) alkoxy C(1-6) alkyl or C(1-6) alkoxyalkyl, C(1-6) alkyloxy carbonyl or C(5-10) aryl,
Y is CH, N or O, —O—$CH_2$—$CH_2$—O— or not present wherein
if Y is O then $R_4$ is not present,
if Y is N then $R_4$ is H, or a C(1-3) alkyl or C(1-3) alkenyl,
if Y is CH then $R_4$ is selected from a H, substituted or unsubstituted C(1-4) alkyl, C(1-4) alkoxy and C(5-10) aryl, $R_3$ is selected from H, a substituted or unsubstituted C(1-6) alkyl, C(1-6) alkoxy, C(1-2) alkoxy C(1-6) alkyl or C(1-6) alkoxyalkyl, C(5-10) aryl $R_5$ is H, C(1-3) alkyl or C(1-3) alkyloxy $R_1$ and $R_2$ are independently H or a C(1-6) alkyl, or $R_1$ and $R_2$ form a 5 or 6 membered, saturated or unsaturated, said ring optionally comprising a heteroatom, or said ring being optionally a substituted or unsubstituted piperidine ring.

16. The method according to claim 12, wherein $Q_1$ is H, halogen, pseudo-halogen, C(1-2) alkyl optionally substituted with 1, 2, 3 or 4 halogen(s), C(1-2) alkoxy, C(5-6) aryl, optionally substituted with 1, 2, 3 or 4 halogen(s), $Q_2$ is H, halogen or pseudo-halogen, X is O, or X has the formula

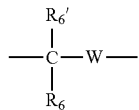

wherein

W is —CH— or carbonyl (—CO—), and $R_6$ and $R_6'$ are independently substituted or unsubstituted C(1-3) alkyl, C(1-3) alkoxy, C(1-2) alkoxy C(1-6) alkyl, C(1-4) alkyloxycarbonyl or at least one of $R_6$ and $R_{6'}$, or $R_6$ and Re together form a C(4-6) cycloalkyl, or X has the formula

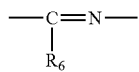

wherein $R_6$ is selected from C(1-3) alkyl, C(1-3) alkoxy, C(1-4) alkoxy C(1-6) alkyl or C(1-6) alkoxyalkyl, C(1-4) alkyloxycarbonyl or C(5-6) aryl, Y is O or —O—CH$_2$—CH$_2$—O— wherein $R_4$ is not present, $R_3$ is selected from H, C(1-4) alkyl, C(1-4) alkoxy, C(1-2) alkoxy C(1-6) alkyl, C(1-6) alkoxyalkyl, or C(5-6) aryl $R_5$ is H, C(1-3) alkyl or C(1-3) alkyloxy $R_1$ and $R_2$ are independently H or a methyl or ethyl, or $R_1$ and $R_2$ form a 5 or 6 membered, saturated or unsaturated ring, said ring optionally comprising a heteroatom, or said ring being optionally a substituted or unsubstituted piperidine ring.

17. The method according to claim 12, wherein the S1R agonist compound has the following formula II:

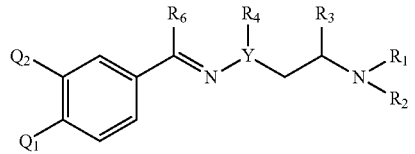

wherein $Q_1$ is a Cl or F or a methyl substituted with halogen selected from CH$_2$F, CHF$_2$CF$_3$, CH$_2$Cl, CHCl$_2$, CCl$_3$, or methoxy $Q_2$ is H, Cl or F, $R_6$ is selected from a substituted or unsubstituted C(1-3) alkyl, C(1-3) alkoxy, C(1-2) alkoxy C(1-6) alkyl, C(5-6) aryl, Y is O $R_4$ is not present, $R_3$ is H, methyl or ethyl, $R_5$ is H, methyl or ethyl, $R_1$ and $R_2$ are independently H, methyl or ethyl, or a pharmaceutically acceptable salt thereof.

18. The method according to claim 12, wherein $Q_1$ is a methyl substituted with halogen selected from CHF$_2$, CF$_3$, CHCl$_2$ and CCl$_3$, $Q_2$ is H, $R_6$ is selected from a substituted or unsubstituted C(1-2) alkoxy C(2-5) alkyl, Y is O, $R_4$ is not present, $R_3$ is H or methyl, $R_5$ is H, methyl or ethyl, $R_1$ and $R_2$ are independently H, methyl or ethyl.

19. The method according to claim 12, wherein the S1R agonist compound is selective for S1 receptors over S2 receptors.

20. The method according to claim 12, wherein the S1R agonist compound is fluvoxamine.

21. The method according to claim 1, wherein treatment of a donor or recipient of the tissue or organ with the S1R agonist compound is avoided, a level of one or more marker(s) selected from the group consisting of number of apoptic cells, expression level of IL-6, and expression level of IL-1α is decreased as compared to a corresponding marker in an organ or tissue stored under identical conditions and in a preservation solution having the same composition but not comprising the S1R agonist compound, and the organ or tissue showed at least 25% less tissue damage as demonstrated by histologic assay after at least 1.5 fold longer preservation time than organs or tissues stored in the same preservation solution not containing the S1R agonist compound.

* * * * *

UNITED STATES PATENT AND TRADEMARK OFFICE
CERTIFICATE OF CORRECTION

PATENT NO. : 12,239,125 B2
APPLICATION NO. : 16/463944
DATED : March 4, 2025
INVENTOR(S) : Fekete et al.

It is certified that error appears in the above-identified patent and that said Letters Patent is hereby corrected as shown below:

In the Claims

In Claim 12, Column 47, approximately Line 15, "$R_6$ and Re" should read -- $R_6$ and $R_6'$ --.

In Claim 16, Column 49, approximately Line 31 or 32, "$R_6$ and Re" should read -- $R_6$ and $R_6'$ --.

Signed and Sealed this
Fifteenth Day of April, 2025

Coke Morgan Stewart
*Acting Director of the United States Patent and Trademark Office*